United States Patent
Pleijers

(10) Patent No.: US 11,278,704 B2
(45) Date of Patent: Mar. 22, 2022

(54) METHOD FOR MANUFACTURING A STEERABLE INSTRUMENT AND SUCH STEERABLE INSTRUMENT

(71) Applicant: Fortimedix Assets II B.V., Geleen (NL)

(72) Inventor: Simon Jozef Arnold Pleijers, Klimmen (NL)

(73) Assignee: Fortimedix Assets II B.V., Geleen (NL)

( * ) Notice: Subject to any disclaimer, the term of this patent is extended or adjusted under 35 U.S.C. 154(b) by 1132 days.

(21) Appl. No.: 15/533,281

(22) PCT Filed: Dec. 5, 2014

(86) PCT No.: PCT/NL2014/050837
§ 371 (c)(1),
(2) Date: Jun. 5, 2017

(87) PCT Pub. No.: WO2016/089202
PCT Pub. Date: Jun. 9, 2016

(65) Prior Publication Data
US 2018/0008805 A1 Jan. 11, 2018

(51) Int. Cl.
*A61M 25/01* (2006.01)
*A61B 17/29* (2006.01)
(Continued)

(52) U.S. Cl.
CPC ....... *A61M 25/0138* (2013.01); *A61B 1/0011* (2013.01); *A61B 1/0055* (2013.01);
(Continued)

(58) Field of Classification Search
CPC ... A61B 1/0011; A61B 1/0055; A61B 1/0057; A61B 17/29; A61B 17/3421;
(Continued)

(56) References Cited

U.S. PATENT DOCUMENTS

2012/0323077 A1  12/2012  Verbeek
2014/0018620 A1   1/2014  Verbeek
(Continued)

FOREIGN PATENT DOCUMENTS

EP   0 764 423 A1   3/1997
EP   0 782 836 A1   7/1997
(Continued)

OTHER PUBLICATIONS

International Search Report, dated Aug. 20, 2015, from corresponding PCT application.

*Primary Examiner* — George J Ulsh
(74) *Attorney, Agent, or Firm* — N.V. Nederlandsch Octrooibureau; Catherine A. Shultz; Katelyn J. Bernier

(57) ABSTRACT

Disclosed is a method for manufacturing a steerable instrument for endoscopic and/or invasive type applications, the instrument including an elongated tubular body having a proximal end part, a distal end part and an intermediate part between proximal and distal end parts, the proximal end part having at least one actuation proximal zone. The distal end part has at least one flexible distal zone, and the elongated tubular body is configured such that a movement of an actuation proximal zone is transferred to a corresponding flexible distal zone for a corresponding movement thereof. The elongated tubular body includes an inner, outer, and intermediate cylindrical elements having longitudinal elements between the inner and outer cylindrical elements. Inner, outer and intermediate cylindrical elements are coupled so movement of an actuation proximal zone is transferred by the longitudinal elements of one of the intermediate cylindrical elements to a corresponding flexible distal zone.

28 Claims, 17 Drawing Sheets

(51) Int. Cl.
  *A61B 17/34* (2006.01)
  *A61B 1/005* (2006.01)
  *A61B 1/00* (2006.01)
  *A61B 17/32* (2006.01)
  *A61M 25/00* (2006.01)
  *A61B 17/00* (2006.01)
  *A61B 90/00* (2016.01)

(52) U.S. Cl.
  CPC ............ *A61B 1/0057* (2013.01); *A61B 17/29* (2013.01); *A61B 17/320016* (2013.01); *A61B 17/3421* (2013.01); *A61M 25/0013* (2013.01); *A61M 25/0147* (2013.01); *A61B 2017/00309* (2013.01); *A61B 2017/00314* (2013.01); *A61B 2017/00323* (2013.01); *A61B 2017/00327* (2013.01); *A61B 2017/291* (2013.01); *A61B 2017/3447* (2013.01); *A61B 2090/037* (2016.02); *A61M 2025/015* (2013.01)

(58) Field of Classification Search
  CPC .......... A61B 90/03; A61B 2017/00309; A61B 2017/00314; A61B 2017/00323; A61B 2017/00327; A61B 2017/3447; A61B 2090/037; A61B 1/00; A61B 1/005; A61B 17/32; A61B 17/34; A61M 25/0013; A61M 25/0138; A61M 25/0147; A61M 2025/015; A61M 25/00; A61M 25/01
  See application file for complete search history.

(56) References Cited

U.S. PATENT DOCUMENTS

| | | |
|---|---|---|
| 2014/0207151 A1 | 7/2014 | Verbeek |
| 2015/0151080 A1* | 6/2015 | Verbeek ............ A61B 17/00234 606/108 |

FOREIGN PATENT DOCUMENTS

| | | |
|---|---|---|
| EP | 1 708 609 A1 | 10/2006 |
| EP | 2 762 058 A1 | 8/2014 |
| WO | 2005/067785 A1 | 7/2005 |
| WO | 2009/112060 A1 | 9/2009 |
| WO | 2009/127236 A1 | 10/2009 |

* cited by examiner

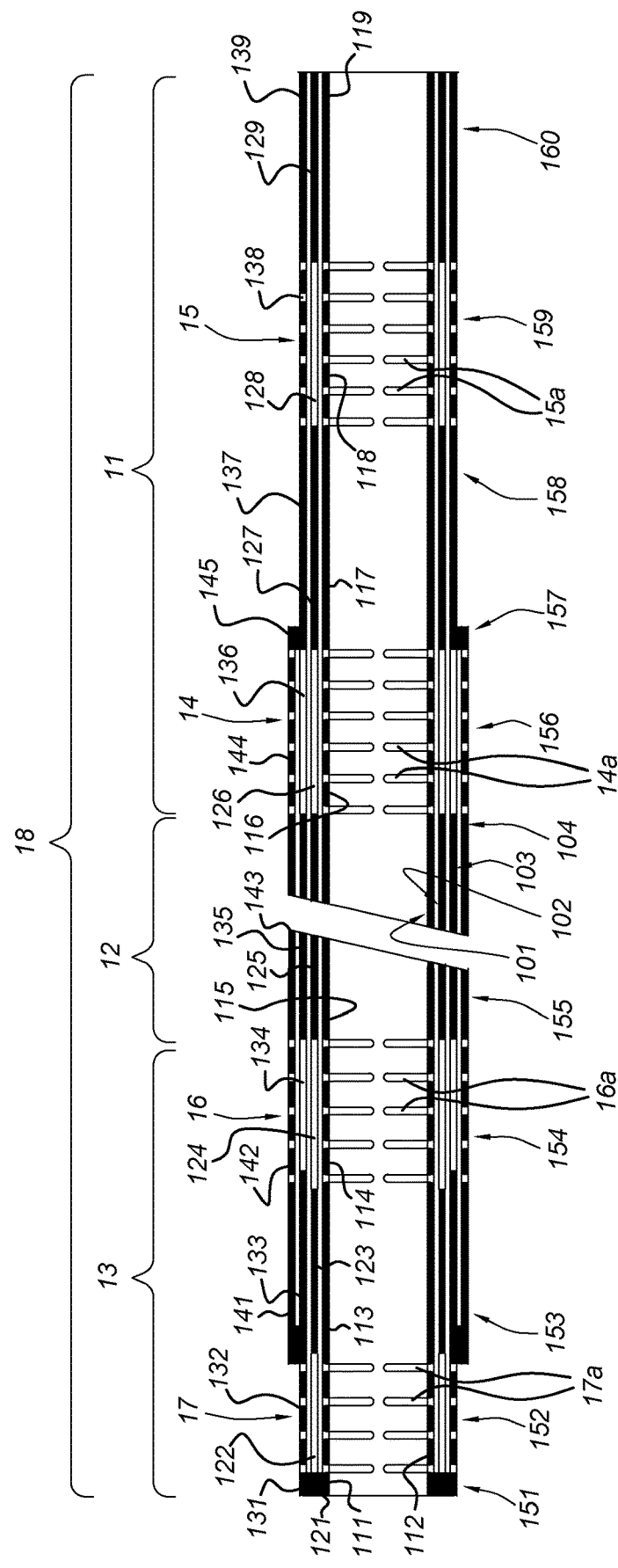

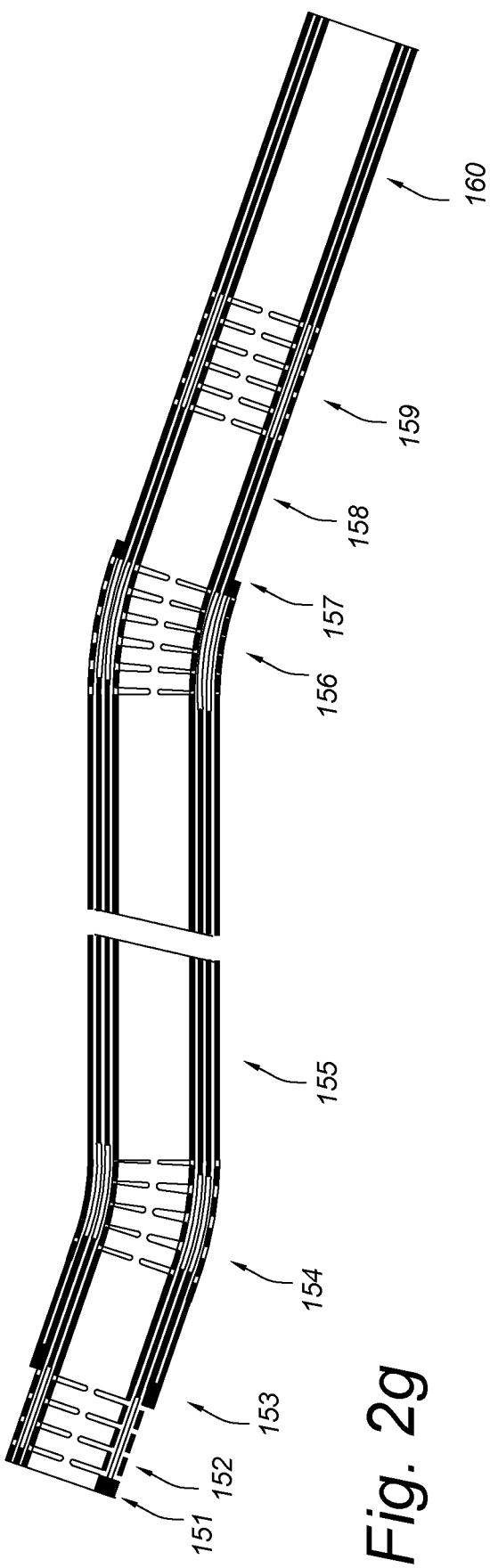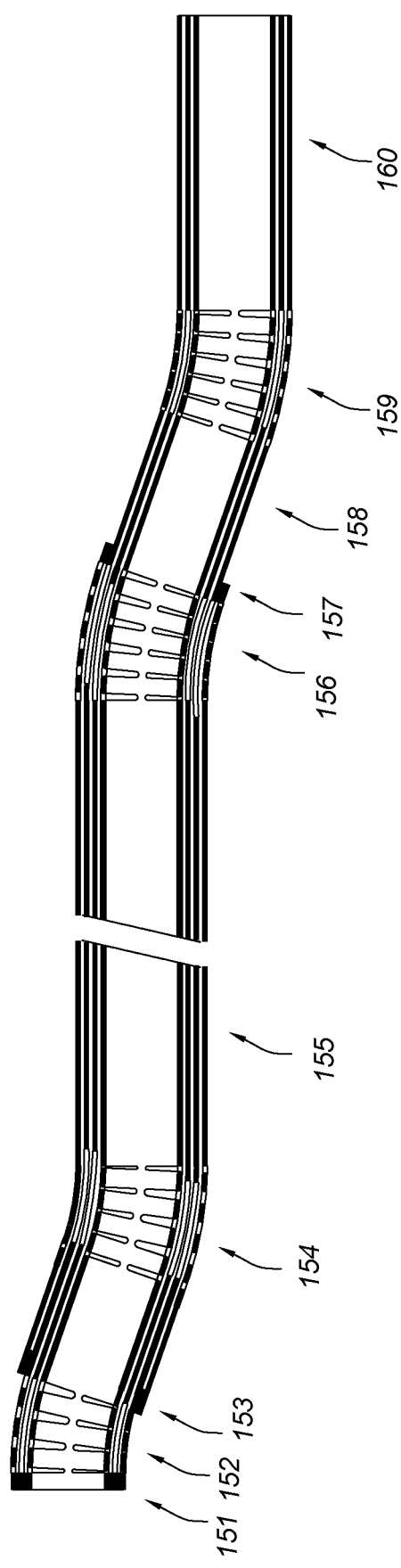

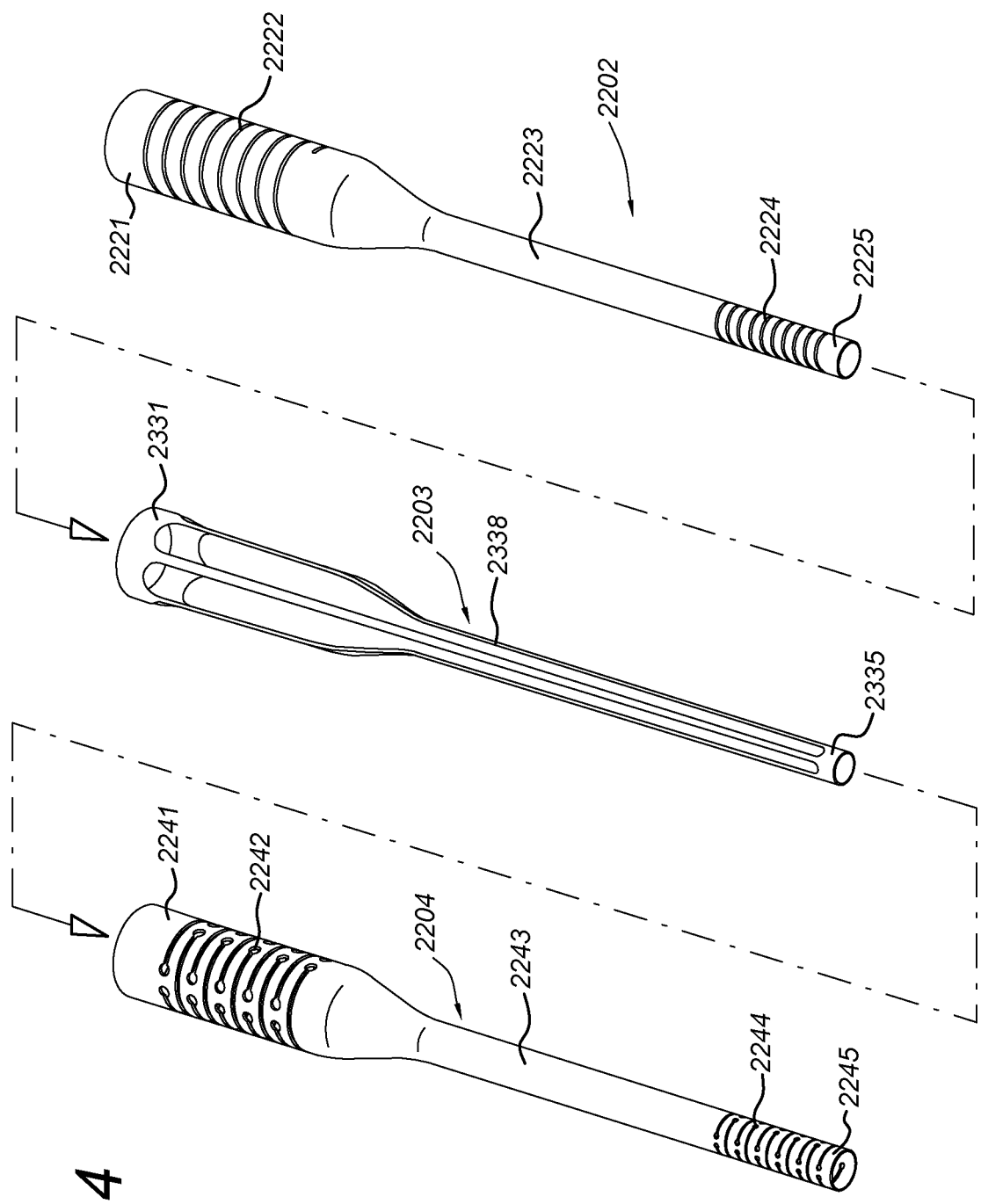

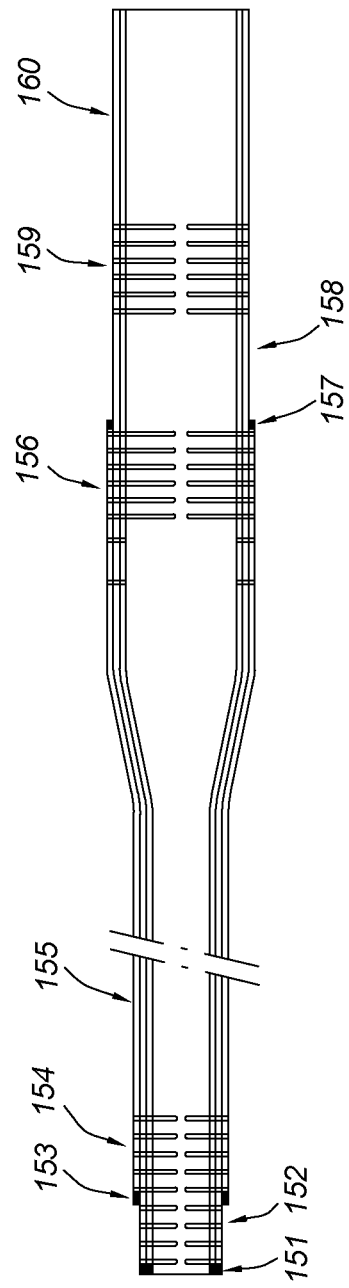
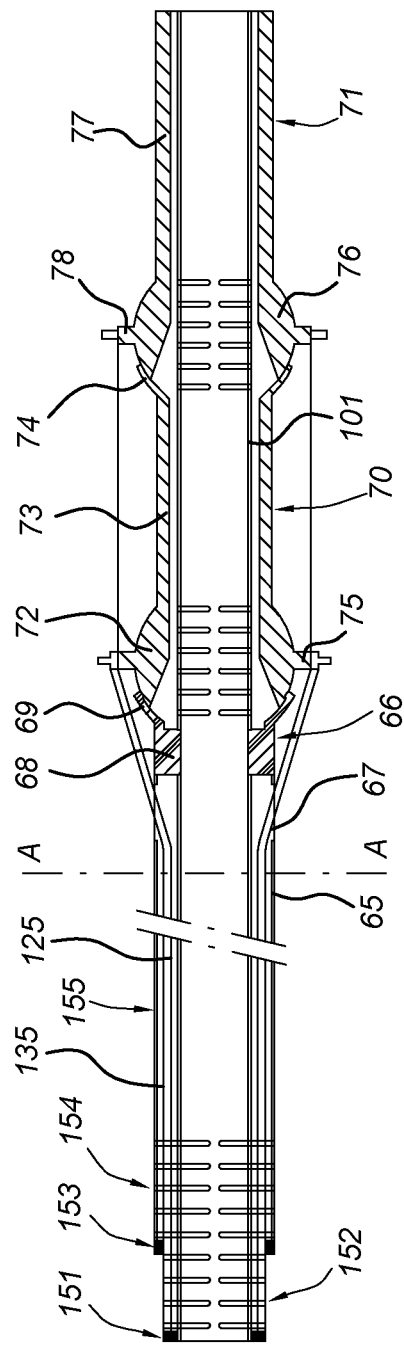

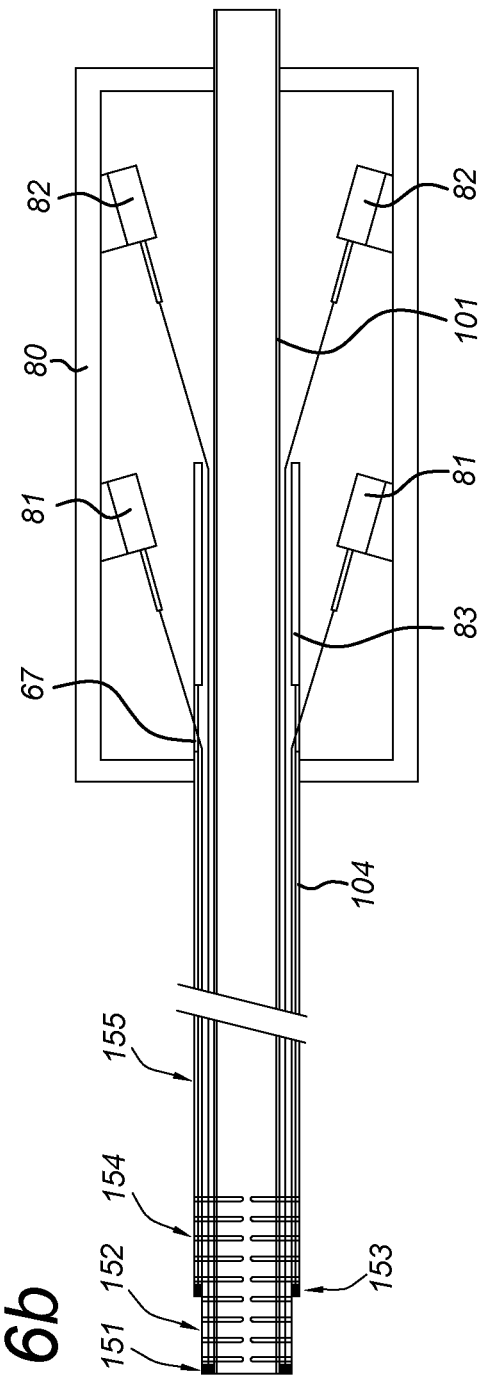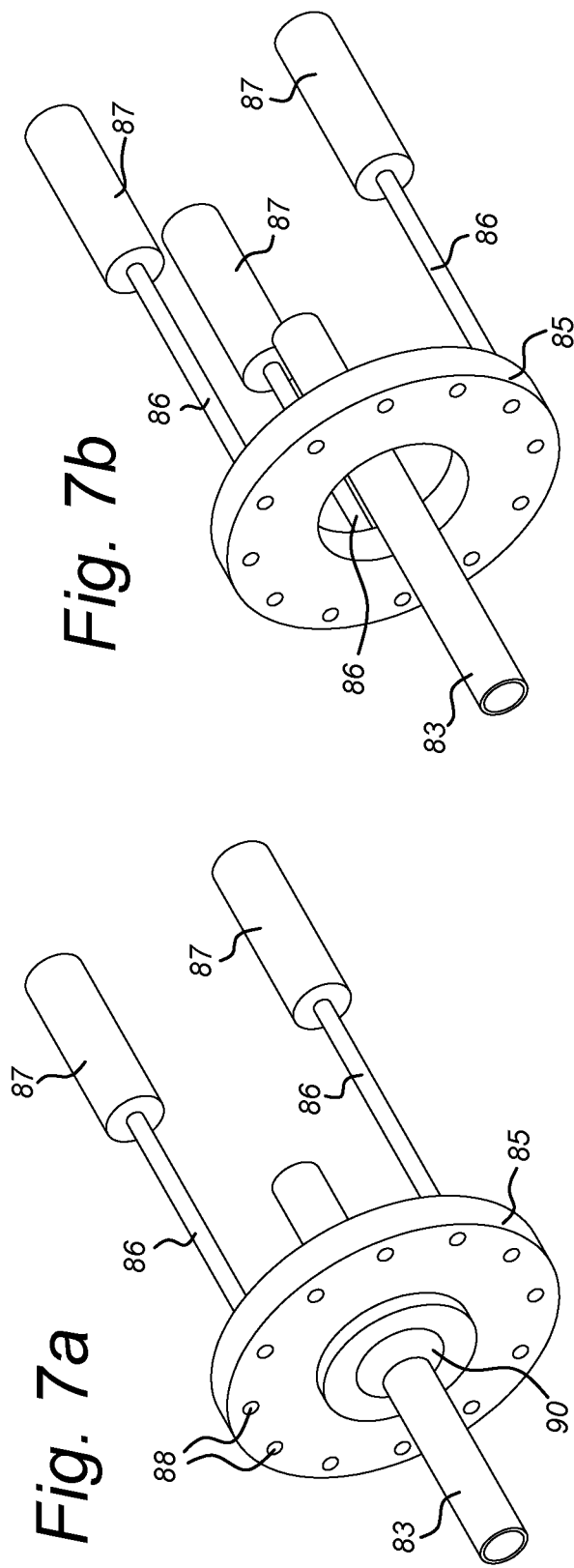

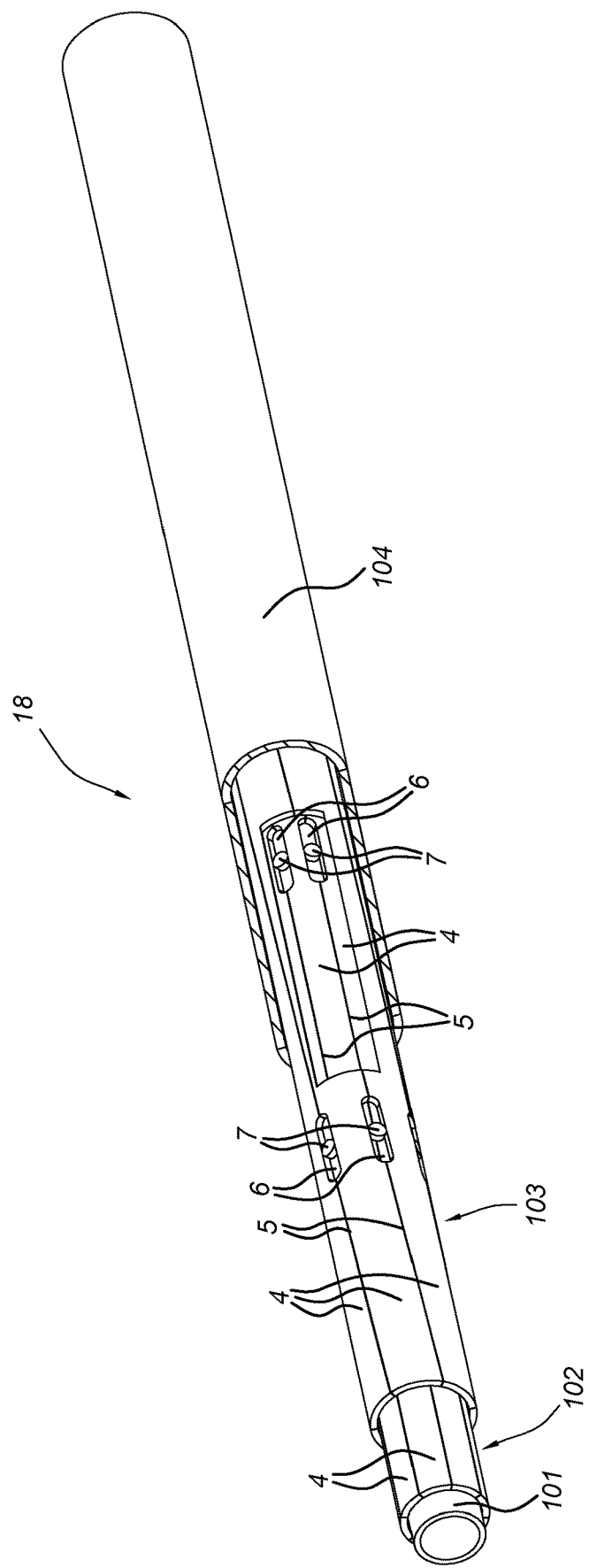

METHOD FOR MANUFACTURING A STEERABLE INSTRUMENT AND SUCH STEERABLE INSTRUMENT

FIELD OF THE INVENTION

The invention relates to a steerable instrument for endoscopic and/or invasive type applications, such as in surgery. The instrument comprises an elongated tubular body having a proximal end part, a distal end part and an intermediate part between proximal and distal end parts, the proximal end part having at least one actuation proximal zone, the distal end part having at least one flexible distal zone, and the elongated tubular body being configured such that a movement of an actuation proximal zone is transferred to a corresponding flexible distal zone for a corresponding movement thereof. The elongated tubular body comprises an inner cylindrical element, an outer cylindrical element and at least one intermediate cylindrical element having longitudinal elements and provided between the inner and outer cylindrical elements, the inner, outer and intermediate cylindrical elements being coupled such that movement of an actuation proximal zone is transferred by the longitudinal elements of one of the intermediate cylindrical elements to a corresponding flexible distal zone.

BACKGROUND OF THE INVENTION

Transformation of surgical interventions that require large incisions for exposing a target area into minimal invasive surgical interventions, i.e. requiring only natural orifices or small incisions for establishing access to the target area, is a well-known and ongoing process. In performing minimal invasive surgical interventions, an operator such as a physician, requires an access device that is arranged for introducing and guiding invasive instruments into the human or animal body via an access port of that body. In order to reduce scar tissue formation and pain to a human or animal patient, the access port is preferably provided by a single small incision in the skin and underlying tissue. In that respect the possibility to use a natural orifice of the body would even be better. Furthermore, the access device preferably enables the operator to control one or more degrees of freedom that the invasive instruments offer. In this way, the operator can perform required actions at the target area in the human or animal body in an ergonomic and accurate manner with a reduced risk of clashing of the instruments used.

Surgical invasive instruments and endoscopes through which these instruments are guided towards the target area are well-known in the art. Both the invasive instruments and endoscopes can comprise a steerable tube that enhances its navigation and steering capabilities. Such a steerable tube preferably comprises a proximal end part including at least one flexible zone, a distal end part including at least one flexible zone, and a rigid intermediate part, wherein the steerable tube further comprises a steering arrangement that is adapted for translating a deflection of at least a part of the proximal end part relative to the rigid intermediate part into a related deflection of at least a part of the distal end part.

Furthermore, the steerable tube preferably comprises a number of co-axially arranged cylindrical elements including an outer element, an inner element and one or more intermediate elements depending on the number of flexible zones in the proximal and distal end parts of the tube and the desired implementation of the steering members of the steering arrangement, i.e. all steering members can be arranged in a single intermediate element or the steering members are divided in different sets and each set of steering members is arranged in a different intermediate member. The steering arrangement may comprise conventional steering cables with sub 1 mm diameters as steering members, wherein the steering cables are arranged between related flexible zones at the proximal and distal end parts of the tube. However, as steering cables have many well-known disadvantages, it is preferred to avoid them and to implement the steering members by one or more sets of longitudinal elements that form integral parts of the one or more intermediate elements. Each of the intermediate elements can be fabricated either by using a suitable material addition technique, such as injection moulding or plating, or by a suitable material removal technique, such as laser cutting, photochemical etching, deep pressing, conventional chipping techniques such as drilling or milling or high-pressure water jet cutting systems. Of the aforementioned material removal techniques, laser cutting is very advantageous as it allows a very accurate and clean removal of material under reasonable economic conditions. Further details regarding the design and fabrication of the abovementioned steerable tube and the steering arrangement thereof have been described for example in WO 2009/112060 A1, WO 2009/127236 A1, U.S. Ser. No. 13/160,949, and U.S. Ser. No. 13/548,935 of the applicant, all of which are hereby incorporated by reference in their entirety.

Steerable invasive instruments typically comprise a handle that is arranged at the proximal end part of the steerable tube for steering the tube and/or for manipulating a tool that is arranged at the distal end part of the steerable tube. Such a tool can for example be a camera, a manual manipulator, e.g. a pair of scissors, forceps, or manipulators using an energy source, e.g. an electrical, ultrasonic or optical energy source.

In this application, the terms "proximal" and "distal" are defined with respect to an operator, e.g. a physician that operates the instrument or endoscope. For example, a proximal end part is to be construed as a part that is located near the physician and a distal end part as a part located at a distance from the physician.

A common single port access device that is used in minimal invasive surgical interventions typically enables to introduce and guide two or more steerable invasive instruments into a human or animal body via a single incision or a natural orifice. For the removal of tissue, typically two steerable instruments are required, wherein a first instrument for example comprising a pair of grasping forceps is used for taking hold of the tissue to be removed and a second instrument for example comprising an electromechanical cutting device is used for dissecting the tissue.

Assembling a steerable instrument having an intermediate cylindrical element in a steerable tube is quite difficult since the longitudinal elements provide the intermediate cylindrical element with a very much decreased bending stiffness. The intermediate cylindrical element with the longitudinal steering elements may deform in a very uncontrolled manner. It easily loses its geometrical coherence. Manipulating the intermediate cylindrical element during and after providing the longitudinal elements therein can become problematic, especially while assembling the steerable tube. This is quite cumbersome when carrying out the assembly, but it may also cause damage to the intermediate cylindrical element. Such damage generally yields a steerable instrument with deteriorated performance, which is very much undesired.

SUMMARY OF THE INVENTION

It is an objective of the invention to provide an efficient and well-controlled method for manufacturing a steerable instrument, and a corresponding steerable instrument and steerable element thereof.

It is another or alternative objective of the invention to provide a method for manufacturing a steerable instrument of which the various elements to be assembled can be manipulated well, and corresponding steerable instrument and steerable element thereof.

It is yet another or alternative objective of the invention to provide a method for manufacturing a steerable instrument that is less vulnerable in causing damage to elements of the steerable instrument, and corresponding steerable instrument and steerable element thereof.

At least one of the above objectives is achieved by a method for manufacturing a steerable instrument for endoscopic and/or invasive type applications, such as in surgery, the instrument comprising an elongated tubular body having a proximal end part, a distal end part and an intermediate part between proximal and distal end parts, the proximal end part having at least one actuation proximal zone, the distal end part having at least one flexible distal zone, and the elongated tubular body being configured such that a movement of an actuation proximal zone is transferred to a corresponding flexible distal zone for a corresponding movement thereof, the elongated tubular body comprising an inner cylindrical element, an outer cylindrical element and at least one intermediate cylindrical element having longitudinal elements and provided between the inner and outer cylindrical elements, the inner, outer and intermediate cylindrical elements being coupled such that movement of an actuation proximal zone is transferred by the longitudinal elements of one of the intermediate cylindrical elements to a corresponding flexible distal zone, wherein the method comprises providing the inner and outer cylindrical elements;

providing an intermediate cylindrical element such that adjacent longitudinal elements are attached to one another at one or more positions distributed along a length of the longitudinal elements by at least one of a releasable attachment and a flexible attachment so as to allow relative movement of the longitudinal elements with respect to one another in a longitudinal direction of the longitudinal elements, after release of attached longitudinal elements in case of a releasable attachment, and so as to restrict movement of longitudinal elements in a radial direction of the intermediate cylindrical element; and incorporating the intermediate cylindrical element between the inner and outer cylindrical elements.

The releasable or flexible connection provides for a connection between adjacent longitudinal elements such that the intermediate cylindrical elements can be handled well for efficient manufacturing of the steerable instrument since movement is restricted in a radial direction. The radial direction is a direction perpendicular to the longitudinal direction of the intermediate cylindrical element, which is an outward and/or inward direction. In case of a releasable connection, the connection is temporal and only present when required during manufacturing of the steerable instrument. During manufacture or afterwards the releasable connection can be released for use of the instrument. A flexible connection may remain after manufacture since it allows longitudinal movement of the longitudinal elements, but keeps the longitudinal elements together since their movement outwards is restricted.

A releasable connection may, for instance, be provided by a wax or glue or the like applied to the intermediate cylindrical element. After insertion or during insertion of the intermediate cylindrical element between inner and outer cylindrical elements, the wax or glue may be removed to release the coupling by heating or treatment with an appropriate agent to remove the wax or glue or the like.

In an embodiment adjacent longitudinal elements are flexibly attached by flexure elements at one or more positions distributed along a length of the longitudinal elements, the flexure elements being configured to provide flexibility thereto so as to allow relative movement of the longitudinal elements with respect to one another in a longitudinal direction while restricting movement of the longitudinal elements in a radial direction. The flexure elements keep the longitudinal elements together in a longitudinal direction, but allow longitudinal movement thereof.

In another embodiment adjacent longitudinal elements are releasably attached by fracture elements at one or more positions distributed along a length of the longitudinal elements, the fracture elements being configured to allow fracture thereof so as to allow relative movement of the longitudinal elements with respect to one another in a longitudinal direction of the longitudinal elements after fracture of the fracture elements. The fracture elements provide for a connection between adjacent longitudinal elements that can be fractured so that longitudinal elements can be moved with respect to one another but of which movement in the radial direction is restricted for a good handling ability. A fracture element may also be fractured by any other means, such as cutting with a suitable scissor or by laser cutting, or even by heating the fracture element.

In an advantageous embodiment the fracture element is shaped such as to provide one or more predetermined fracture locations where the fracture element will fracture upon application of a suitable force. Such fracture locations do provide well-defined fractures and fracture forces required to break the fracture element.

In an embodiment fracture elements are fractured after having incorporated the intermediate cylindrical element between inner and outer cylindrical elements by applying a force onto adjacent longitudinal elements such as to induce movement of the longitudinal elements with respect to one another and to fracture the fracture elements. Inserting the intermediate cylindrical element between inner and outer cylindrical elements while the fracture elements are still intact provides a good handling of the intermediate cylindrical element en yields a fast and reliable manufacturing of the steerable instrument. The fracture elements remain within the instrument after fracture but are enclosed by the inner, outer and intermediate cylindrical elements so as to remain trapped.

In another embodiment the force is applied to the longitudinal elements by applying a force to an actuation proximal zone or a flexible distal zone. Having assembled the inner, outer and intermediate cylindrical elements while the fracture elements are still intact, it only requires a simple action to act upon the flexible zones to break the fracture elements. Moving the flexible zones is what the steerable instrument is designed to do. Using this capability is therefore easy and efficient to break the fracture elements.

In yet another embodiment a fracture element is fractured, and optionally removed, when incorporating the intermediate cylindrical element between inner and outer cylindrical elements. In some circumstances it may be more suited to break the fracture elements during the process of inserting the intermediate cylindrical element between inner and outer cylindrical elements. The part of the intermediate cylindrical element that has already been inserted has the fracture elements fractured, and optionally removed, while the part not yet inserted is still firm enough to be handled well for further insertion between inner and outer cylindrical elements.

In another aspect the invention provides an intermediate cylindrical element for use in a method for manufacturing a steerable instrument for endoscopic and/or invasive type applications and/or for application in a steerable instrument for endoscopic and/or invasive type applications, the intermediate cylindrical element comprising longitudinal elements of which adjacent ones are attached by at least one of one or more fracture and one or more flexure elements at one or more positions distributed along a length of the longitudinal elements. The fracture or flexure elements can be configured in various ways. In embodiments they may first show flexibility so that they act as a flexure element, but fracture after some time to have become a fracture element.

In an embodiment adjacent longitudinal elements are separated by slits, and one or more slits are bridged by one or more fracture or flexure elements at one or more positions distributed along a length of the longitudinal elements. Such fracture elements will take the form of tiny bridge elements. They can be efficiently obtained. The slits are generally made by a process like laser cutting. A part of the slit can be left uncut to provide a fracture element. The fracture or flexure element can be provided with a smaller thickness than the wall thickness of the intermediate cylindrical element to tune fracture or flexure characteristics of the fracture element.

In an embodiment the slit is dimensioned such that movement of a longitudinal element is guided by adjacent longitudinal elements when provided in a steerable instrument, by which movement of the longitudinal elements during use of the steerable instrument is well controlled.

In an advantageous embodiment a gap is provided between adjacent longitudinal elements along at least a part of a length of the adjacent longitudinal elements, and the at least one of one or more and one or more flexure elements is provided in the gap. The gap can generally be provided as an extension and a wider part of the slit between adjacent longitudinal elements. A fracture or flexure element having a larger length, as measured in a direction perpendicular to a longitudinal direction of the longitudinal elements, can be provided in such gap. This allows larger force moments to be exerted on the fracture elements, which may assist in breaking the fracture elements when moving the longitudinal elements, or provide an enhanced flexibility in case of flexure elements. A width of the gap may correspond to 5%-95% of the width of a longitudinal element as measured in a direction perpendicular to the longitudinal direction of the longitudinal elements.

In an embodiment the at least one or more fracture elements have a substantially constant width in a longitudinal direction of the longitudinal elements and a length in a direction perpendicular to the longitudinal direction of the longitudinal elements. A length over width ratio of the fracture element is preferably larger than 4, in embodiment larger than 8. Such fracture element is relatively simple and easily provided. Dependent on the material used and on its dimensions it may fracture upon a force by the longitudinal elements or it may be fractured (broken) by cutting the fracture element. Cutting can be done by mechanical means, such as suitable scissors, or by laser cutting or the like.

In another embodiment the at least one of one or more fracture and one or more flexure elements has at least one of the following shapes: one or more Z-shapes and one or more S-shapes. The Z-shape or S-shape can be made to have flexibility in the longitudinal direction of the longitudinal elements so as to allow movement thereof, while their movement in radial direction is restricted. The Z-shape therefore may provide a flexible connection between adjacent longitudinal elements. In other embodiments in may be formed as a Z-shaped fracture element.

In an advantageous embodiment the at least one or more fracture elements are shaped such as to provide one or more predetermined fracture locations where the at least one or more fracture elements will fracture upon application of a suitable force. Having such predefined fracture locations yields an improved control over the fracture characteristics of the fracture elements. Fracturing thus becomes very reliable.

In an embodiment the at least one or more fracture elements have a width in a longitudinal direction of the longitudinal elements, a length in a direction perpendicular to the longitudinal direction of the longitudinal elements and ends, each end being attached to a respective one of the adjacent longitudinal elements, the width of the at least one or more fracture elements decreasing from a central area of the fracture elements along their lengths towards their ends such that the ends provide fracture locations. A maximum force moment is applied at these locations when moving the longitudinal elements. Making the fracture element weakest at these point by providing the smallest width at the connections of the fracture element with the longitudinal elements allows the fracture element to become disconnected from both longitudinal elements for a smooth movement control of the longitudinal elements after fracture of the fracture elements.

In preferred embodiments the at least one or more fracture elements have a substantially elliptical shape, or a substantially circular shape. Such shape of the fracture elements will yield both a shear force and a tensile force on the fracture element for enhanced fracture characteristics. This is especially the case for the circular shape, which roll between both adjacent longitudinal elements when they are moved with respect to one another.

In yet other embodiments the at least one or more fracture elements have a width in a longitudinal direction of the longitudinal elements, a length in a direction perpendicular to the longitudinal direction of the longitudinal elements and ends, each end being attached to a respective one of the adjacent longitudinal elements, the width of the at least one or more fracture elements decreasing from the ends of the at least one or more fracture elements along their lengths towards a central area of the at least one or more fracture elements, such that the central area provides a fracture location. This proved a single fracture location somewhere in the middle of the fracture element. This is especially advantageous in circumstances in which a detached fracture element is undesirable.

In a preferred embodiment the at least one or more fracture elements are substantially hour-glass shaped. The at least one or more fracture elements may be shaped such that they comprise two substantially triangular shaped members attached at their tops, two substantially semi-elliptical shaped members attached at their semi-elliptical circumference, or two substantially semi-circular shaped members attached at their semi-circular circumference.

In yet another aspect the invention provides a steerable instrument for endoscopic and/or invasive type applications, the instrument comprising an elongated tubular body having a proximal end part, a distal end part and an intermediate part between proximal and distal end parts, the proximal end part having at least one actuation proximal zone, the distal end part having at least one flexible distal zone, and the elongated tubular body being configured such that a movement of an actuation proximal zone is transferred to a corresponding flexible distal zone for a corresponding movement thereof, the elongated tubular body comprising an inner cylindrical element, an outer cylindrical element and at least one intermediate cylindrical element having longitudinal elements and provided between the inner and outer cylindrical elements, the inner, outer and intermediate cylindrical elements being coupled such that movement of an actuation proximal zone is transferred by the longitudinal elements of one of the intermediate cylindrical elements to a corresponding flexible distal zone, and the at least one intermediate cylindrical element being an intermediate cylindrical element referred to above and having fractured, removed or not yet fractured fracture elements in case of fracture elements attaching adjacent longitudinal elements.

Preferably, the fracture elements are distributed such along a length of the intermediate cylindrical element that the fracture elements do not interfere with one or more parts of an adjacent cylindrical element. The fracture elements then will not obstruct functioning of the steerable instrument, especially when fracture elements have become detached from their longitudinal elements.

In an embodiment in which at least two adjacent intermediate cylindrical elements are provided, the fracture elements are distributed such along a length of the intermediate cylindrical elements that a fracture element of one intermediate cylindrical element does not interfere with one or more fracture elements of an adjacent intermediate cylindrical element.

In an embodiment of the method, intermediate cylindrical element or instrument an actuation proximal zone can be configured as a flexible proximal zone.

In yet another embodiment of the method, intermediate cylindrical element or steerable instrument comprising fracture elements, each fracture element is configured and arranged to fracture when adjacent longitudinal elements, to which each such fracture element is attached, are moved in a longitudinal direction relative to one another such as to develop an actual fracture element stress in each such fracture element which is larger than or equal to the ultimate tensile stress of each individual fracture element, while, at the same time, the actual fracture element stress as developed in each one of these adjacent longitudinal elements remains lower than their own respective yield stresses.

BRIEF DESCRIPTION OF THE DRAWINGS

Further features and advantages of the invention will become apparent from the description of the invention by way of non-limiting and non-exclusive embodiments. These embodiments are not to be construed as limiting the scope of protection. The person skilled in the art will realize that other alternatives and equivalent embodiments of the invention can be conceived and reduced to practice without departing from the scope of the present invention. Embodiments of the invention will be described with reference to the figures of the accompanying drawings, in which like or same reference symbols denote like, same or corresponding parts, and in which:

FIG. 2e shows a longitudinal cross-sectional view of the elongated tubular body of the steerable instrument as shown in FIG. 2c.

FIG. 2f shows a longitudinal cross-sectional view of the elongated tubular body of the steerable instrument as shown in FIG. 2c, wherein the first proximal and first distal flexible zones are bent, thereby illustrating the operation of the steering arrangement.

FIG. 2g shows a longitudinal cross-sectional view of the elongated tubular body of the steerable instrument as shown in FIG. 2f, wherein additionally the second proximal and second distal flexible zones are bent, thereby further illustrating the operation of the steering arrangement.

FIG. 4 shows a perspective exploded view of three cylindrical elements of a steerable tube analogous to the exploded view of FIG. 2j, but with a varying diameter of the cylindrical elements.

FIG. 5 shows a schematic cross-section of a steerable tube with cylindrical elements comparable as shown in FIGS. 3a, 3b and 3c.

FIGS. 6a and 6b show schematic cross-sections of further embodiments of a steerable tube with inner, intermediate and outer cylindrical elements.

FIGS. 7a and 7b show schematic perspective views of actuators that can be used with a steerable tube.

FIG. 17 shows an embodiment of an assembly of two intermediate cylindrical elements between inner and outer cylindrical elements, of which both intermediate cylindrical elements have longitudinal elements and fracture elements.

DETAILED DESCRIPTION OF EMBODIMENTS

Figure 1:
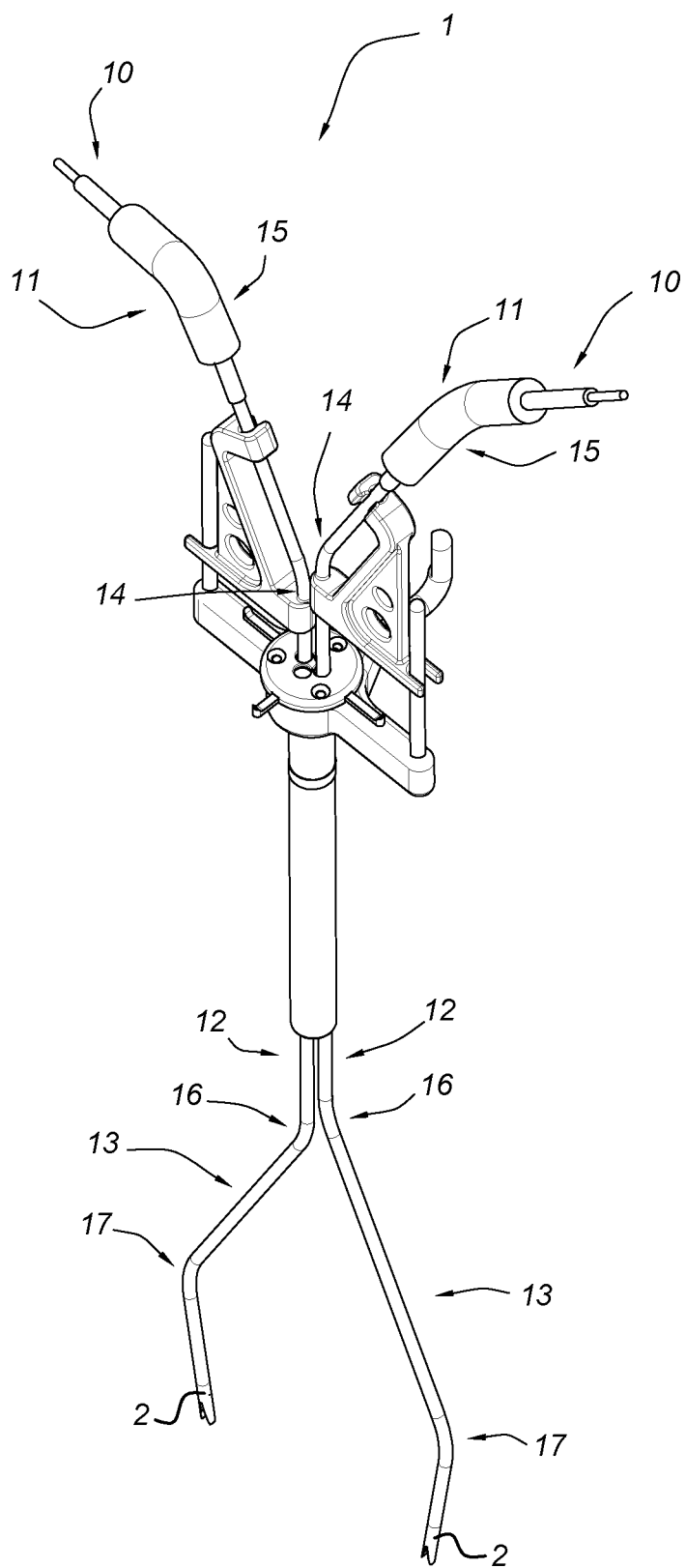
FIG. 1 shows a schematic perspective view of a non-limiting embodiment of a invasive instrument assembly having two steerable instruments.
Figure 2A:
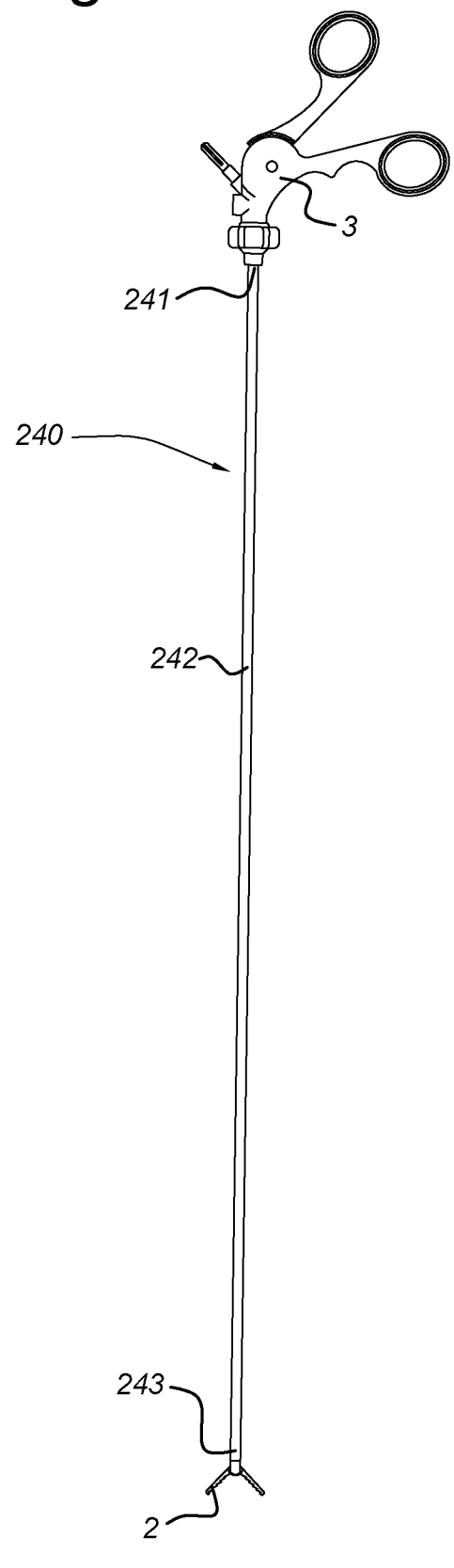
FIG. 2a shows a side view of a non-limiting embodiment of a rigid invasive instrument.
Figure 2B:
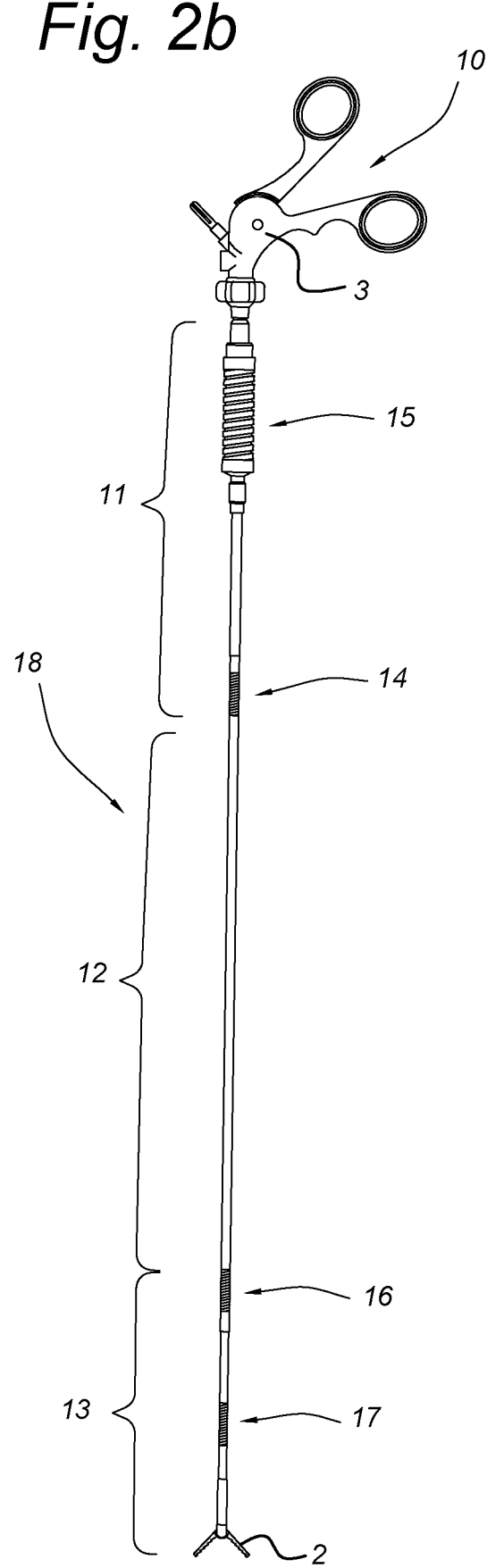
FIG. 2b shows a side view of a non-limiting embodiment of a steerable invasive instrument.

FIG. 2a shows a side view of a non-limiting embodiment of a rigid invasive instrument 240 and FIG. 2b shows a non-limiting embodiment of a steerable invasive instrument 10. FIG. 1 shows a non-limiting embodiment of an invasive instrument assembly 1 having an introducer with two such steerable invasive instruments 10, which introducer is known from the prior art. Details of the non-limiting embodiment of the steerable invasive instruments 10 are explained in relation to FIGS. 2c to 2k.

The rigid invasive instrument 240 as shown in FIG. 2a comprises an elongated shaft 242 having a proximal end part 241 and a distal end part 243. At the distal end part 243 a tool 2, for example a forceps, is arranged. At the proximal end part 241 a handle 3 is arranged that is adapted for manipulating the tool 2, i.e. opening and closing the jaw of the forceps. To that effect, a control rod (not shown) is present within the elongated shaft 242, which rod connects the handle 3 with the tool 2. The rod can be moved by the handle 3 and the movement of the rod is translated into a predetermined movement of the tool 2, as is known to persons skilled in the art and need no further explanation here. Also, the shaft 242 may comprise conducting wires to allow a current to flow to a tool, e.g. to heat said tool in order to perform a heat treatment within a human or animal body.

FIG. 2b shows a side view of a steerable invasive instruments 10. The steerable instrument 10 comprises an elongated tubular body 18 having a proximal end part 11 including two actuation proximal zones 14, 15, a distal end part 13 including two flexible distal zones 16, 17, and a rigid intermediate part 12. The actuation proximal zones 14, 15 in the present embodiment are configured as flexible proximal zones, and will further be referred to as flexible proximal zones. At the distal end part 13 a tool, like a forceps 2 is arranged. At the proximal end part 11 a handle 3 is arranged that is adapted for opening and closing the jaw of the forceps 2.

Figure 2C:
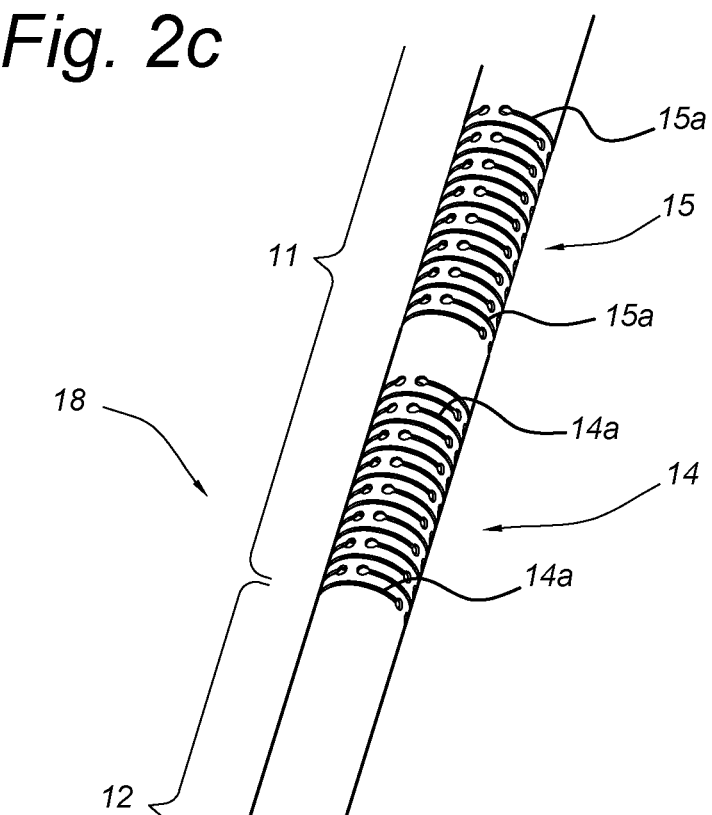
FIG. 2c provides a detailed perspective view of a non-limiting embodiment of the elongated tubular body of the steerable instrument.

FIG. 2c provides a detailed perspective view of the distal portion of the elongated tubular body 18 of the steerable instrument 10 and shows that the elongated tubular body 18 comprises of a number of co-axially arranged layers or cylindrical elements including an outer cylindrical element 104 that ends after the first flexible distal zone 16 at the distal end portion 13. The distal end portion 13 of the outer cylindrical element 104 is fixedly attached to the cylindrical element 103 located within and adjacent to the outer cylindrical element 104, e.g. by means of spot welding at welding spots 100. However, any other suitable attachment method can be used, including gluing by a suitable glue.

Figure 2D:
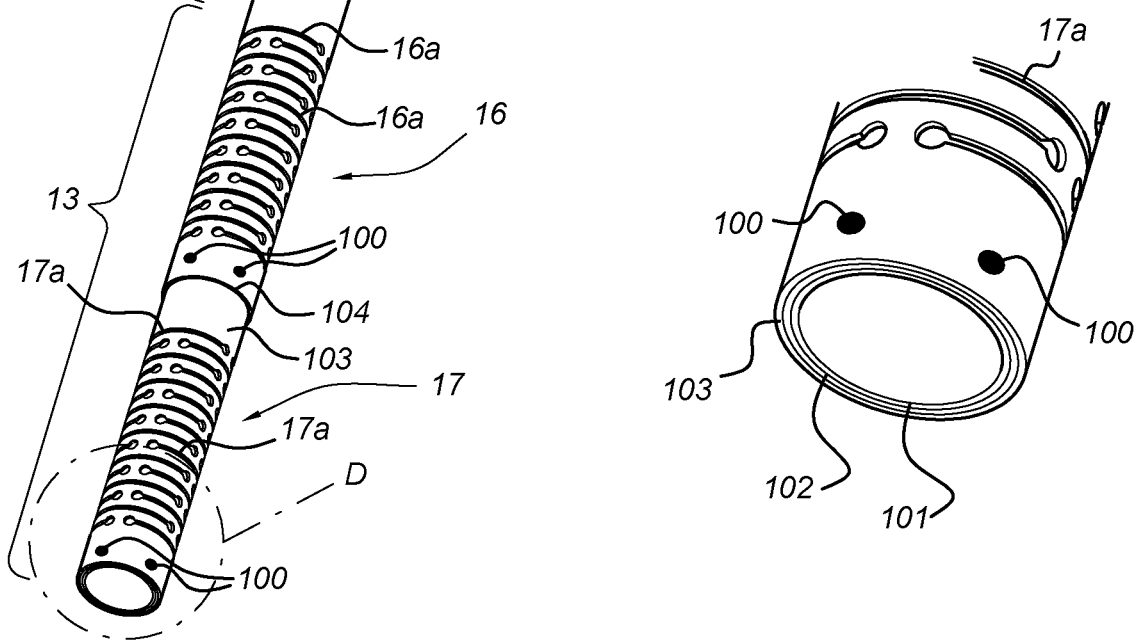
FIG. 2d provides a more detailed view of the distal end part of the elongated tubular body as shown in FIG. 2c.

FIG. 2d provides a more detailed view of the distal end part 13 and shows that it includes three co-axially arranged layers or cylindrical elements being an inner cylindrical element 101, a first intermediate cylindrical element 102 and a second intermediate cylindrical element 103. The distal ends of inner cylindrical element 101, first intermediate cylindrical element 102 and second intermediate cylindrical element 103 are all three fixedly attached to one another. This may be done by means of spot welding at welding spots 100. However, any other suitable attachment method can be used, including gluing by a suitable glue. The points of attachment may be at the end edges of inner cylindrical element 101, first intermediate cylindrical element 102 and second intermediate cylindrical element 103, as shown in the figures. However, these points of attachment may also be located some distance away from these edges, be it, preferably, between the end edges and the locations of the flexible zone 17.

It will be clear to the skilled person that the elongated tubular body 18 as shown in FIG. 2c comprises four cylindrical elements in total. The elongated tubular body 18 according to the embodiment shown in FIG. 2c comprises two intermediate cylindrical elements 102 and 103 in which the steering members of the steering arrangement are arranged. The steering arrangement in the exemplary embodiment of the elongated tubular body 18 as shown in FIG. 2c comprises the two flexible zones 14, 15 at the proximal end part 11 of the elongated tubular body 18, the two flexible zones 16, 17 at the distal end part 13 of the elongated tubular body 18 and the steering members that are arranged between related flexible zones at the proximal 11 and distal 13 end parts. An exemplary actual arrangement of the steering members is shown in FIG. 2e, which provides a schematic longitudinal cross-sectional view of the exemplary embodiment of the elongated tubular body 18 as shown in FIG. 2c.

FIG. 2e shows the four layers or cylindrical elements mentioned above, i.e. the inner cylindrical element 101, the first intermediate cylindrical element 102, the second intermediate cylindrical element 103, and the outer cylindrical element 104.

The inner cylindrical element 101, as seen along its length from the distal end to the proximal end of the instrument, comprises a rigid ring 111, which is arranged at the distal end part 13 of the steerable instrument 10, a first flexible portion 112, a first intermediate rigid portion 113, a second flexible portion 114, a second intermediate rigid portion 115, a third flexible portion 116, a third intermediate rigid portion 117, a fourth flexible portion 118, and a rigid end portion 119, which is arranged at the proximal end portion 11 of the steerable instrument 10.

The first intermediate cylindrical element 102, as seen along its length from the distal end to the proximal end of the instrument, comprises a rigid ring 121, a first flexible portion 122, a first intermediate rigid portion 123, a second flexible portion 124, a second intermediate rigid portion 125, a third flexible portion 126, a third intermediate rigid portion 127, a fourth flexible portion 128, and a rigid end portion 129. The longitudinal dimensions of the rigid ring 121, the first flexible portion 122, the first intermediate rigid portion 123, the second flexible portion 124, the second intermediate rigid portion 125, the third flexible portion 126, the third intermediate rigid portion 127, the fourth flexible portion 128, and the rigid end portion 129 of the first intermediate element 102, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the inner cylindrical element 101, respectively, and are coinciding with these portions as well. In this description "approximately equal" means that respective same dimensions are equal within a margin of less than 10%, preferably less than 5%.

The second intermediate cylindrical element 103, as seen along its length from the distal end to the proximal end of the instrument, comprises a first rigid ring 131, a first flexible portion 132, a second rigid ring 133, a second flexible portion 134, a first intermediate rigid portion 135, a first intermediate flexible portion 136, a second intermediate rigid portion 137, a second intermediate flexible portion 138, and a rigid end portion 139. The longitudinal dimensions of the first rigid ring 131, the first flexible portion 132 together with the second rigid ring 133 and the second flexible portion 134, the first intermediate rigid portion 135, the first intermediate flexible portion 136, the second intermediate rigid portion 137, the second intermediate flexible portion 138, and the rigid end portion 139 of the second intermediate cylinder 103, respectively, are aligned with, and preferably approximately equal to the longitudinal dimensions of the rigid ring 111, the first flexible portion 112, the first intermediate rigid portion 113, the second flexible portion 114, the second intermediate rigid portion 115, the third flexible portion 116, the third intermediate rigid portion 117, the fourth flexible portion 118, and the rigid end portion 119 of the first intermediate element 102, respectively, and are coinciding with these portions as well.

The outer cylindrical element 104, as seen along its length from the distal end to the proximal end of the instrument, comprises a first rigid ring 141, a first flexible portion 142, a first intermediate rigid portion 143, a second flexible portion 144, and a second rigid ring 145. The longitudinal dimensions of the first flexible portion 142, the first intermediate rigid portion 143 and the second flexible portion 144 of the outer cylindrical element 104, respectively, are aligned with, and preferably approximately equal to the longitudinal dimension of the second flexible portion 134, the first intermediate rigid portion 135 and the first intermediate flexible portion 136 of the second intermediate element 103, respectively, and are coinciding with these portions as well. The rigid ring 141 has approximately the same length as the rigid ring 133 and is fixedly attached thereto, e.g. by spot welding or gluing. Preferably, the rigid ring 145 overlaps with the second intermediate rigid portion 137 only over a length that is required to make an adequate fixed attachment between the rigid ring 145 and the second intermediate rigid portion 137, respectively, e.g. by spot welding or gluing. The rigid rings 111, 121 and 131 are attached to each other, e.g., by spot welding or gluing. This may be done at the end edges thereof but also at a distance of these end edges.

In an embodiment, the same may apply to the rigid end portions 119, 129 and 139, which can be attached together as well in a comparable manner. However, as will be explained hereinafter, the construction may be such that the diameter of the cylindrical elements at the proximal portion is larger, or smaller, with respect to the diameter at the distal portion. In such embodiment the construction at the proximal portion differs from the one shown in FIG. 2e. As a result of the increase in diameter an amplification is achieved, i.e., the bending angle of a flexible zone at the distal portion will be larger than the bending angle of a corresponding flexible portion at the proximal portion. This will be further described below with reference to FIG. 4.

The inner and outer diameters of the cylindrical elements 101, 102, 103, and 104 are chosen in such a way at a same location along the elongated tubular body 18 that the outer diameter of inner cylindrical element 101 is slightly less than the inner diameter of the first intermediate cylindrical element 102, the outer diameter of the first intermediate cylindrical element 102 is slightly less than the inner diameter of the second intermediate cylindrical element 103 and the outer diameter of the second intermediate cylindrical element 103 is slightly less than the inner diameter of the outer cylindrical element 104, in such a way that a sliding movement of the adjacent cylindrical elements with respect to each other is possible. The dimensioning should be such that a sliding fit is provided between adjacent elements. A clearance between adjacent elements may generally be in the order of 0.02 to 0.1 mm, but depends on the specific application and material used. The clearance preferably is smaller than a wall thickness of the longitudinal elements to prevent an overlapping configuration thereof. Restricting the clearance to about 30% to 40% of the wall thickness of the longitudinal elements is generally sufficient.

As can be seen in FIG. 2e, flexible zone 14 of the proximal end part 11 is connected to the flexible zone 16 of the distal end part 13 by portions 134, 135 and 136, of the second intermediate cylindrical element 103, which form a first set of longitudinal steering members of the steering arrangement of the steerable instrument 10. Furthermore, flexible zone 15 of the proximal end part 11 is connected to the flexible zone 17 of the distal end part 13 by portions 122, 123, 124, 125, 126, 127, and 128 of the first intermediate cylindrical element 102, which form a second set of longitudinal steering members of the steering arrangement. The use of the construction as described above allows the steerable instrument 10 to be used for double bending. The working principle of this construction will be explained with respect to the examples shown in FIGS. 2f and 2g.

For the sake of convenience, as shown in FIGS. 2e, 2f and 2g, the different portions of the cylindrical elements 101, 102, 103, and 104 have been grouped into zones 151-160 that are defined as follows. Zone 151 comprises the rigid rings 111, 121, and 131. Zone 152 comprises the portions 112, 122, and 132. Zone 153 comprises the rigid rings 133 and 141 and the portions 113 and 123. Zone 154 comprises the portions 114, 124, 134 and 142. Zone 155 comprises the portions 115, 125, 135 and 143. Zone 156 comprises the portions 116, 126, 136 and 144. Zone 157 comprises the rigid ring 145 and the parts of the portions 117, 127, and 137 coinciding therewith. Zone 158 comprises the parts of the portions 117, 127, and 137 outside zone 157. Zone 159 comprises the portions 118, 128 and 138. Finally, zone 160 comprises the rigid end portions 119, 129 and 139.

In order to deflect at least a part of the distal end part 13 of the steerable instrument 10, it is possible to apply a bending force, in any radial direction, to zone 158. According to the examples shown in FIGS. 2f and 2g, zone 158 is bent downwards with respect to zone 155. Consequently, zone 156 is bent downwards. Because of the first set of steering members comprising portions 134, 135, and 136 of the second intermediate cylindrical element 103 that are arranged between the second intermediate rigid portion 137 and the second rigid ring 133, the downward bending of zone 156 is transferred by a longitudinal displacement of the first set of steering members into an upward bending of zone 154 with respect to zone 155. This is shown in both FIGS. 2f and 2g.

It is to be noted that the exemplary downward bending of zone 156, only results in the upward bending of zone 154 at the distal end of the instrument as shown in FIG. 2f. Bending of zone 152 as a result of the bending of zone 156 is prevented by zone 153 that is arranged between zones 152 and 154. When subsequently a bending force, in any radial direction, is applied to the zone 160, zone 159 is also bent. As shown in FIG. 2g, zone 160 is bent in an upward direction with respect to its position shown in FIG. 2f. Consequently, zone 159 is bent in an upward direction. Because of the second set of steering members comprising portions 122, 123, 124, 125, 126, 127 and 128 of the first intermediate cylindrical element 102 that are arranged between the rigid ring 121 and the rigid end portion 129, the upward bending of zone 159 is transferred by a longitudinal displacement of the second set of steering members into a downward bending of zone 152 with respect to its position shown in FIG. 2f.

FIG. 2g further shows that the initial bending of the instrument in zone 154 as shown in FIG. 2f will be maintained because this bending is only governed by the bending of zone 156, whereas the bending of zone 152 is only governed by the bending of zone 159 as described above. Due to the fact that zones 152 and 154 are bendable independently with respect to each other, it is possible to give the distal end part 13 of the steerable instrument 10 a position and longitudinal axis direction that are independent from each other. In particular the distal end part 13 can assume an advantageous S-like shape. In known instruments such as described in EP 1 708 609 A, the position and the direction of the longitudinal axis are always coupled and cannot be individually controlled. The skilled person will appreciate that the capability to independently bend zones 152 and 154 with respect to each other, significantly enhances the maneuverability of the distal end part 13 and therefore of the steerable instrument 10 as a whole.

Obviously, it is possible to vary the lengths of the flexible portions shown in FIGS. 2e to 2g as to accommodate specific requirements with regard to bending radii and total lengths of the distal end part 13 and the proximal end part 11 of the steerable instrument 10 or to accommodate amplification or attenuation ratios between bending of at least a part of the proximal end part 11 and at least a part of the distal end part 13.

The steering arrangement of the steerable invasive instrument 10 may comprise conventional steering cables as steering members that are fixedly attached to the respective rigid rings 121, 133. However due to well-known disadvantages of conventional steering cables, the steering members preferably comprise one or more sets of longitudinal elements that form integral parts of the one or more intermediate cylindrical elements 102, 103. Preferably, the longitudinal elements comprise remaining parts of the wall of an intermediate cylindrical element 102, 103 after the wall of the intermediate cylindrical element 102, 103 has been provided with longitudinal slits that define the remaining longitudinal steering elements.

Figure 2H:
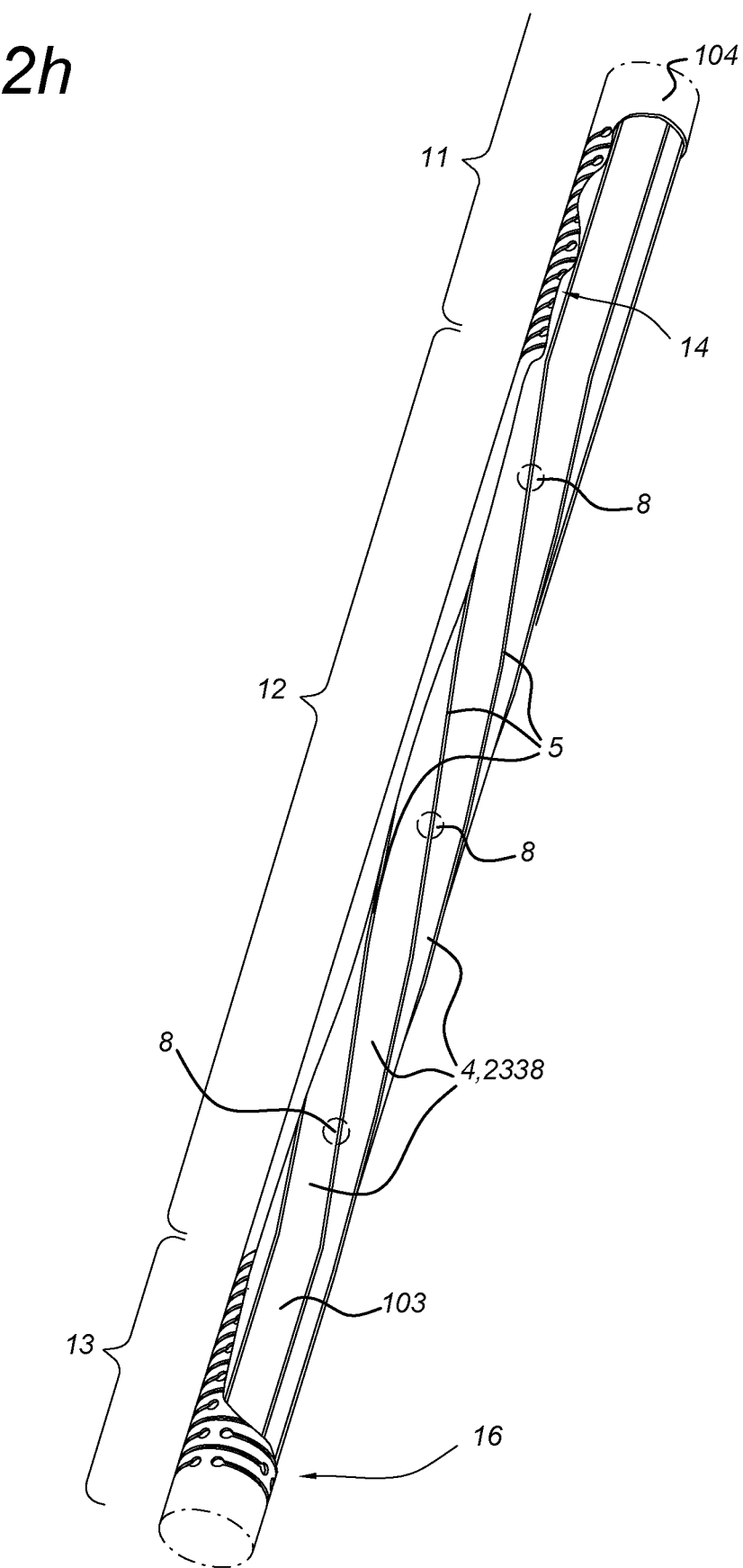
FIG. 2h shows a perspective view of a part of the elongated tubular body as shown in FIG. 2c, wherein the outer cylindrical element partially has been removed to show an exemplary embodiment of the longitudinal steering elements that have been obtained after providing longitudinal slits to the wall of an intermediate cylindrical element that interconnects the first proximal flexible zone and the first distal flexible zone of the elongated tubular body.
Figure 2I:
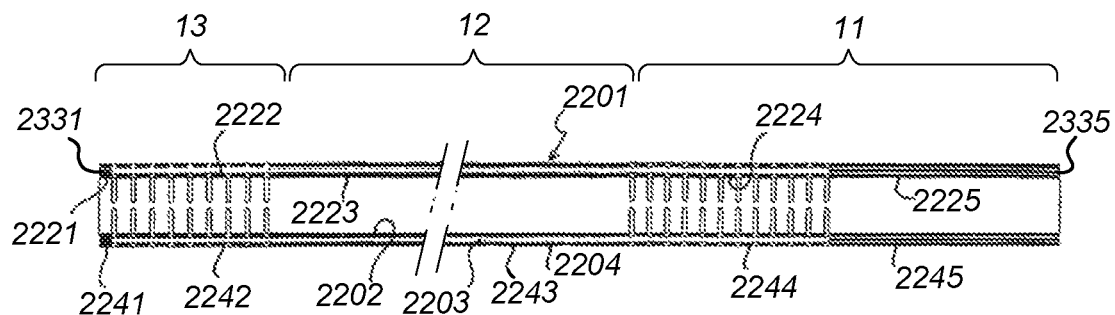
FIG. 2i shows a longitudinal cross-sectional view of an exemplary embodiment of a steerable instrument having one proximal and one distal flexible zone.
Figure 2J:
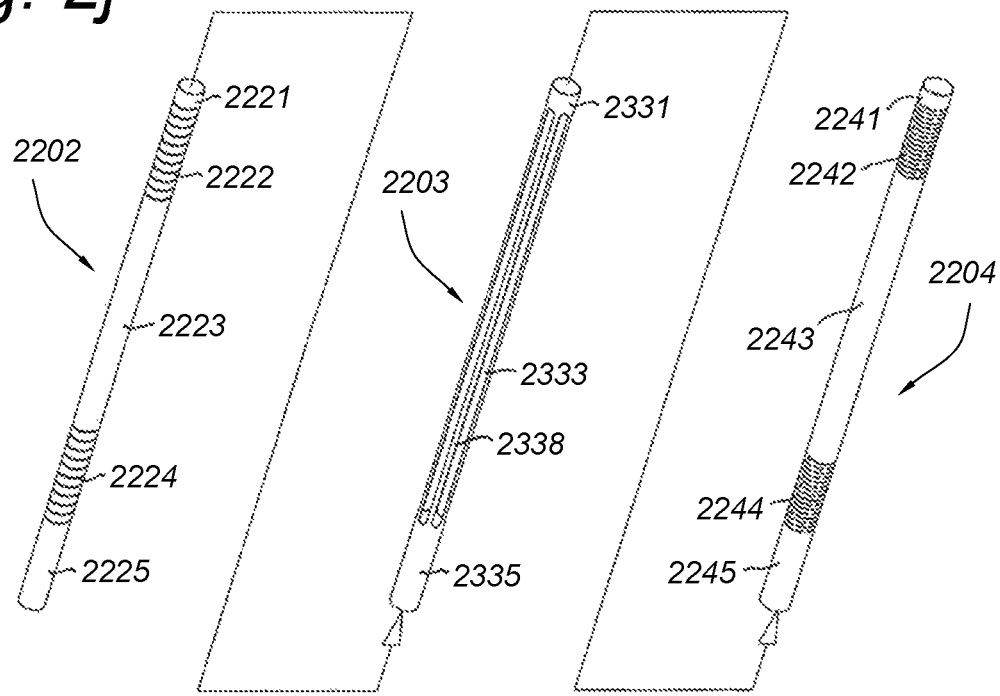
FIG. 2j shows a perspective exploded view of the three cylindrical elements of the steerable instrument shown in FIG. 2i.
Figure 2K:
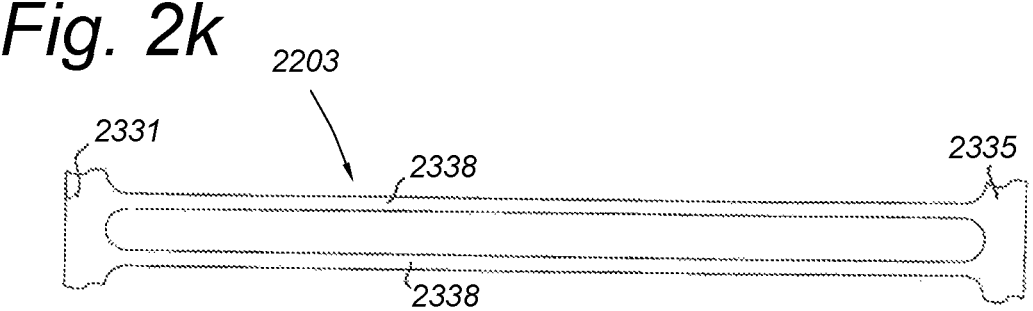
FIG. 2k shows a top view of an unrolled version of an exemplary embodiment of the intermediate cylindrical element of the steerable instrument shown in FIG. 2j. The intermediate cylindrical element can be formed by rolling the unrolled version into a cylindrical configuration and attaching adjacent sides of the rolled-up configuration by any known attaching means such as by a welding technique.

Further details regarding the fabrication of the latter longitudinal steering elements are provided with reference to FIGS. 2i to 2k regarding an exemplary embodiment of a steerable instrument that comprises only one flexible zone at both its proximal 11 and distal end 13 parts.

FIG. 2i shows a longitudinal cross-section of a steerable instrument 2201 comprising three co-axially arranged cylindrical elements, i.e. inner cylindrical element 2202, intermediate cylindrical element 2203 and outer cylindrical element 2204. The inner cylindrical element 2202 comprises a first rigid end part 2221, which is located at the distal end part 13 of the instrument 2201, a first flexible part 2222, an intermediate rigid part 2223, a second flexible part 2224 and a second rigid end part 2225, which is located at the proximal end part 11 of the instrument 2201.

The outer cylindrical element 2204 also comprises a first rigid end part 2241, a first flexible part 2242, an intermediate rigid part 2243, a second flexible part 2244 and a second rigid end part 2245. The lengths of the different parts of the cylindrical elements 2202 and 2204 are substantially the same so that when the inner cylindrical element 2202 is inserted into the outer cylindrical element 2204, the different parts are positioned against each other.

The intermediate cylindrical element 2203 also has a first rigid end part 2331 and a second rigid end part 2335 which in the assembled condition are located between the corresponding rigid parts 2221, 2241 and 2225, 2245 respectively of the two other cylindrical elements 2202, 2204. The intermediate part 2333 of the intermediate cylindrical element 2203 comprises three or more separate longitudinal elements which can have different forms and shapes as will be explained below. After assembly of the three cylindrical elements 2202, 2203 and 2204 whereby the element 2202 is inserted in the element 2203 and the two combined elements 2202, 2203 are inserted into the element 2204, at least the first rigid end part 2221 of the inner cylindrical element 2202, the first rigid end part 2331 of the intermediate cylindrical element 2203 and the first rigid end part 2241 of the outer cylindrical element 2204 at the distal end of the instrument are attached to each other. In the embodiment shown in FIGS. 2i and 2j, also the second rigid end part 2225 of the inner cylindrical element 2202, the second rigid end part 2335 of the intermediate cylindrical element 2203 and the second rigid end part 2245 of the outer cylindrical element 2204 at the proximal end of the instrument are attached to each other such that the three cylindrical elements 2202, 2203, 2204 form one integral unit.

In the embodiment shown in FIG. 2j the intermediate part 2333 of intermediate cylindrical element 2203 comprises a number of longitudinal elements 2338 with a uniform cross-section so that the intermediate part 2333 has the general shape and form as shown in the unrolled condition of the intermediate cylindrical element 2203 in FIG. 2k. From FIG. 2k it also becomes clear that the intermediate part 2333 is formed by a number of over the circumference of the intermediate cylindrical part 2203 equally spaced parallel longitudinal elements 2338. Advantageously, the number of longitudinal elements 2338 is at least three, so that the instrument 2201 becomes fully controllable in any direction, but any higher number is possible as well. Preferably, the number of longitudinal elements 2338 is 6 or 8.

The production of such an intermediate part is most conveniently done by injection moulding or plating techniques or starting from a cylindrical tube with the desired inner and outer diameters and removing parts of the wall of the cylindrical tube required to end up with the desired shape of the intermediate cylindrical element 2203. However, alternatively, any 3D printing method can be used.

The removal of material can be done by means of different techniques such as laser cutting, photochemical etching, deep pressing, conventional chipping techniques such as drilling or milling, high pressure waterjet cutting systems or any suitable material removing process available. Preferably, laser cutting is used as this allows for a very accurate and clean removal of material under reasonable economic conditions. The above mentioned processes are convenient ways as the member 2203 can be made so to say in one process, without requiring additional steps for connecting the different parts of the intermediate cylindrical member as required in the conventional instruments, where conventional steering cables must be connected in some way to the end parts. The same type of technology can be used for producing the inner and outer cylindrical elements 2202 and 2204 with their respective flexible parts 2222, 2224, 2242 and 2244.

FIG. 2h shows an exemplary embodiment of longitudinal (steering) elements 4 that have been obtained after providing longitudinal slits 5 to the wall of the second intermediate cylindrical element 103 that interconnects proximal flexible zone 14 and distal flexible zone 16 as described above. I.e., longitudinal steering elements 4 are, at least in part, spiraling about a longitudinal axis of the instrument such that an end portion of a respective steering element 4 at the proximal portion of the instrument is arranged at another angular orientation about the longitudinal axis than an end portion of the same longitudinal steering element 4 at the distal portion of the instrument. Were the longitudinal steering elements 4 arranged in a linear orientation, than a bending of the instrument at the proximal portion in a certain plane would result in a bending of the instrument at the distal portion in the same plane but in a 180 degrees opposite direction. This spiral construction of the longitudinal steering elements 4 allows for the effect that bending of the instrument at the proximal portion in a certain plane may result in a bending of the instrument at the distal portion in another plane, or in the same plane in the same direction. A preferred spiral construction is such that the end portion of a respective steering element 4 at the proximal portion of the instrument is arranged at an angular shifted orientation of 180 degrees about the longitudinal axis relative to the end portion of the same longitudinal steering element 4 at the distal portion of the instrument. However, e.g. any other angular shifted orientation, e.g. 90 degrees, is within the scope of this document. The slits are dimensioned such that movement of a longitudinal element is guided by adjacent longitudinal elements when provided in place in a steerable instrument.

The flexible portions 112, 132, 114, 142, 116, 144, 118, and 138 as shown in FIG. 2e, as well as the flexible parts 2222, 2224, 2242, and 2244 shown in FIGS. 2i and 2j can be obtained by the methods described in the European patent application 08 004 373.0 filed on 10 Mar. 2008, page 5, lines 15-26, but any other suitable process can be used to make flexible portions.

Such flexible parts may have a structure as shown in FIGS. 2c and 2d. I.e., the flexibility may be obtained by a plurality of slits 14a, 15a, 16a, 17a. E.g., two circumferential slits may be provided in a cylindrical element along a same circumferential line where both slits are located at a certain distance from one another. A plurality of identical sets of circumferential slits 14a, 15a, 16a, 17a is provided at a plurality of distances in the longitudinal direction of the instrument, where consecutive sets are arranged at an angular rotated position, e.g. each time 90 degrees rotated. In such an arrangement, all parts of the cylindrical element are still connected to each other.

Figure 3A:
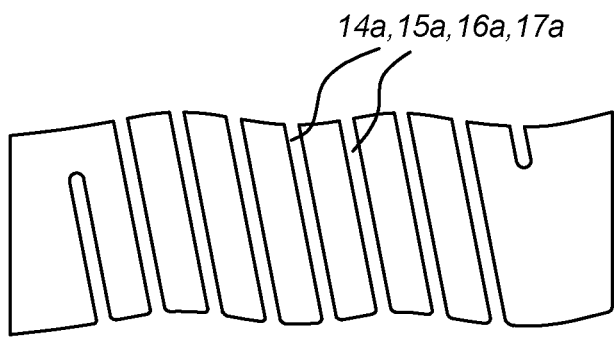
FIGS. 3a, 3b and 3c show schematic representation of unrolled views of embodiments of flexible proximal and distal parts of inner, outer and intermediate cylindrical elements.
Figure 3B:
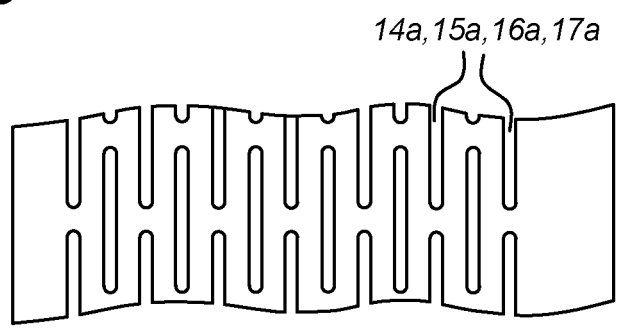
Figure 3C:
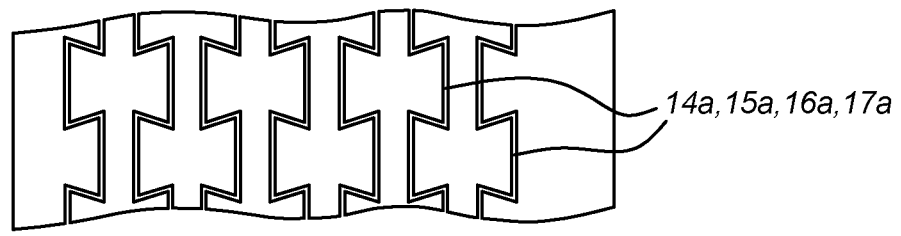

FIGS. 3a, 3b and 3c show alternative manners of how such flexibility in part can be obtained. FIG. 3a shows a schematic representation of a flat rolled-out flexible proximal or distal cylindrical zone. The intermediate cylindrical elements are then made by rolling-up the flat element and attaching the side edges together in any suitable fashion that is known as such, such as by a welding technique. In the embodiment shown in FIG. 3a, the part of the cylindrical tube to become flexible has been provided with slits 14a, 15a, 16a, 17a extending in a helical manner over the length of the flexible zone. The flexibility can be controlled by the number of slits and/or the angle of the slits with respect to the axial direction of the cylindrical member. In the embodiment of FIG. 3b the part of the cylindrical tube to become flexible has been provided with a number of short slits 14a, 15a, 16a, 17a. The slits can be divided into groups, the slits in each group being located in the same line extending perpendicular to the axis of the cylindrical member. The slits of two neighboring groups are offset. In the embodiment of FIG. 3c the part of the cylindrical tube to become flexible has been provided by making slits 14a, 15a, 16a, 17a producing a number of swallow's tails between the slits, which fit into each other as shown. It will be obvious that other systems of providing a flexible zone in a cylindrical tube wall may be used as well. More specifically it is possible to use combinations of the systems shown above. However, any other suitable flexible construction may be used instead. For instance, any of the flexible constructions shown and described in EP 0 764 423 A and EP 0 782 836 A may be used as well.

Furthermore, if the portions 122, 123, 124, 125, 126, 127, and 128 of the first intermediate cylindrical element 102 and the portions 134, 135, and 136 of the second intermediate cylindrical element 103 that respectively form the first and second set of longitudinal steering members, as shown in FIG. 2e, are implemented as longitudinal steering elements 4 as shown in FIG. 2h, the fabrication methods described above can be used. The same applies to the longitudinal elements 2338 of FIGS. 2j and 2k. Moreover, any embodiment described in EP 2 762 058 A can be used according to the invention.

Otherwise, the longitudinal elements 4, 2338 can also be obtained by any other technique known in the art such as for example described in EP 1 708 609 A. The only restriction with respect to the construction of the longitudinal elements used in these portions is that the total flexibility of the instrument in these locations where the flexible portions coincide must be maintained.

The different co-axially arranged layers or cylindrical elements 101, 102, 103, 104, 2202, 2203 and 2204 as described above in relation to the exemplary embodiments of the steerable instruments shown in FIGS. 2e and 2i, respectively, may be produced by any of the known methods, provided that they are suitable to make a multilayer system. A multilayer system is to be understood as being a steerable instrument that comprises at least two separate sets of longitudinal elements 4, 2338 for transferring the movement of the proximal end part to the distal end part. The assembly of the different cylindrical elements can be realized in the same way as well. Preferred methods of producing the different cylindrical elements have been described in the above mentioned EP 2 762 058 A which is hereby incorporated by reference in its entirety.

In the above embodiments, the proximal portions and distal portions are constructed in a similar way. However, that need not be the case always as will be explained now.

E.g., the proximal portion may have a wider diameter as shown in FIG. 4, which shows a special embodiment of an instrument according to the invention. The inner cylindrical element 2202 is composed of a first rigid end part 2225, a first flexible part 2224, an intermediate rigid part 2223, a second flexible part 2222 and a second rigid end part 2221 which is normally used as the operating part of the instrument in that it serves to steer the other end of the unit. The outer cylindrical element 2204 is in the same way composed of a first rigid part 2245, a flexible part 2244, an intermediate rigid part 2243, a second flexible part 2242 and a second rigid part 2241. The intermediate cylindrical element 2203 also has a first rigid end part 2335 and a second rigid end part 2331 which in the assembled condition are located between the corresponding rigid parts 2225, 2245 and 2221, 2241, respectively, of the two other cylindrical elements 2202, 2204. In the embodiment shown the longitudinal elements 2338 are of the type shown in FIG. 2j, but it will be obvious that any other type described above may be used as well. So far the construction is comparable to the instruments described above. The main difference with respect to the above embodiments is the use of a different set of diameters for some parts of the instrument. In the embodiment shown in FIG. 4 the parts 2222, 2221, 2331, 2242 and 2241 have a larger diameter than the other parts. In the parts 2223, 2338 and 2243 frusto-conical portions have been made in order to connect the small diameter parts with the large diameter parts. As shown in FIG. 4 the different parts can easily be assembled by inserting one into the other. The main reason, however, to have such an instrument with different diameters is that by using an operating part with a larger diameter, the movement of the other end is amplified, whereas if a smaller diameter is used the movement of the other end is reduced. Dependent of the application and its requirements larger diameters can be used to have the amplified movement or smaller diameters can be used to reduce the movement and increase accuracy.

Such widening of the instrument with increasing diameter towards the proximal portions can also be applied in an instrument with more than two bendable portions, as shown in FIGS. 5 to 7b. In FIG. 5 there is shown an instrument having four layers and as such the instrument is comparable to the instrument of FIG. 2e but the actuating portion of the cylindrical elements has a larger diameter compared to the handling end portion and in the zone 155 a frusto-conical part has been incorporated. As a result of the larger diameter of the actuating portion at the proximal end the movement of the handling portion at the distal end will be amplified upon bending, thereby amplifying the movement of the handling head. It is also possible to work in the opposite direction with a handling portion at the distal end with a larger diameter than the actuating portion at the proximal end, whereby the degree of movement is decreased, thereby improving accuracy of movement of the handling head In FIG. 6a there is shown an embodiment of an instrument according to the invention which is comparable to the instrument as shown in FIG. 5 in which the movement of the actuating portions is amplified into a movement of the handling portion. Here also there is shown an instrument having four layers as in the instrument of FIGS. 2e and 5.

The left hand side with respect to the line A-A of the instrument as shown in FIG. 6a, which is the handling (distal) end portion, is completely identical to the left hand side including distal end part 13 and partly intermediate rigid part 12 of the instrument as shown in FIG. 2e. The right hand side with respect to the line A-A of the instrument as shown in FIG. 6a has been modified. The inner layer or cylindrical element 101 can be completely identical to the inner cylindrical element 101 shown in FIG. 2e. The outer layer or cylindrical element at the right hand side of the line A-A has been modified in that it consists of a rigid portion 65 connected to the left hand side and an end portion 66 connected to the right hand side. The rigid portion 65 is formed by a cylindrical element having a number of slits 67 parallel to the axis of the instrument and regularly spaced around the circumference of the portion 65. The end portion 66 comprises a cylindrical bush 68 provided with a ring flange 69 forming a spherical flange.

The right hand side of the instrument is further composed of two actuating members 70 and 71. The actuating member 70 is a hollow tube like element comprising a ball shaped member 72, a tube 73 and a spherical flange 74. The ball shaped member 72 fits into the spherical flange 69 and in this way the member 70 is rotatably connected to the left hand part of the instrument. The ball shaped member 72 is provided with an annular flange surrounding the same and having two sets of openings, a first set positioned along a circle line around the flange 75 and a second set also positioned along a circle line around the flange 75, the circle line of the first set preferably having a same diameter as the circle line of the second set. The actuating member 71 is also a hollow tube like element comprising a ball shaped member 76 and a tube 77. The ball shaped member 76 is comparable to the ball shaped member 72 and fits into the spherical flange 74 whereby the member 71 is rotatably connected to the member 70. The ball shaped member 76 is provided with an annular flange 78 surrounding the same and provided with a set of openings positioned along a circle line around the flange 78. The area of the instrument comprising the ring/spherical flange 69 and ball shaped member 72 is an actuation zone of the instrument, and the area of the instrument comprising the ring/spherical flange 74 and ball shaped member 76 is another actuation zone of the instrument.

The left hand part of the first intermediate layer or cylindrical element 102 comprises the longitudinal elements of the portion 125. In the right hand part with respect to the line A-A, these longitudinal elements are guided through some of the slits 67, through the first set of openings in the flange 75 and into the openings in the flange 78 to which they are connected. The left hand part of the second intermediate layer or cylindrical element 103 comprises the longitudinal elements of the portion 135. In the right hand part with respect to the line A-A these longitudinal elements are guided through some of the slits 67 into the second set of openings in the flange 75 to which they are connected. The operation of the instrument shown in FIG. 6a is comparable to the operation of the instrument of FIG. 2e. Any bending movement of the member 70 with respect to the flange 69 is translated into a bending movement of the zone 154, and any bending movement of the member 71 with respect to the flange 74 is translated into a bending movement of the zone 152. As a result of the fact that the longitudinal elements controlling the bending are connected to the actuating members 70 and 71 at points having a greater distance to the longitudinal axis of the instrument than the corresponding elements at the other end of the instrument, the bending movement of the members 70 and 71 is amplified into a bigger bending movement of the zones 154 and 152, respectively, and as such its operation is comparable to that of the instrument of FIG. 5.

In the embodiment shown in FIG. 6b the handling end portion is identical to the handling end portion of the embodiment shown in FIG. 6a, whereas the actuating end portion has been modified. Around the actuating end portion there is provided a cylindrical housing 80 which is mounted on the external layer or outer cylindrical element 104 of the instrument. Furthermore, the external layer of the instrument at the actuating end portion side is provided with a cylindrical member 83 such that between the zone 155 and the cylindrical member 83 a number of slits 67 are present as also shown in FIG. 6a. To the inner wall of the cylindrical housing 80 there are mounted two sets of linear actuators 81 and 82, respectively. A linear actuator is a device which can cause a translation movement of an element such as, for example, the longitudinal elements in this type of endoscopic instruments. Such linear actuators are generally known in the art and will not be described in more detail here, and they can be controlled by electronic devices such as computers.

The longitudinal elements of the outer (second) intermediate layer 103 are passing through the slits 67 and connected to the set 81 of linear actuators. The longitudinal elements of the inner (first) intermediate layer 102 are passing through the cylindrical member 83 and connected to the second set 82 of linear actuators. By means of an appropriate actuation of the linear actuators 81 and 82 the orientation of the flexible zones 152 and 154 can be changed so that the same effects are obtained as with the instrument according to FIG. 6*a* or FIG. 2*e*, which means that more curves can be made by the handling end portion. It is necessary that the actuation of the different linear actuators is done in a controlled manner as otherwise the change of orientation cannot be carried out. This means that if one actuator 81 is exerting a pulling force on its corresponding longitudinal element, the other actuators must be acting in a corresponding way, which means either exerting a smaller pulling force or exerting a pushing force so that the whole is in balance. The same applies if both sets of actuators are activated simultaneously. The areas of the instrument comprising the linear actuators are respective actuation zones of the instrument in the present embodiment.

In case the number of longitudinal elements is larger than three, which is mostly required to have a smooth transition of the movement of the actuating end portion to the handling end portion, the electronic control of all linear actuators may become complicated. In the FIGS. 7*a* and 7*b* there are shown two solutions for such a system. In the embodiment of FIG. 7*a* a disc 85 is mounted movable on the cylindrical element 83 by means of a ball bearing 90. The disc 85 is provided with a number of openings 88 along its outer circumference and the longitudinal elements are connected to the disc through these openings. As such the operation of the disc 85 is comparable to that of the disc 75 in FIG. 6*a*. Two of the openings 88 are connected through elements 86 to a linear actuator 87. If the two openings 88 are not diametrically opposed to each other with respect to the axis of the cylindrical member 83, the movement of the two actuators 87 is sufficient to control fully the orientation of the disc 85 and thereby the movement imposed on the corresponding zone of the handling end portion.

In the embodiment shown in FIG. 7*b* the disc 85 is not supported by a ball bearing on the cylindrical member 83, but three of the openings 88 are through elements 86 connected to linear actuators 87 and also supported by that. These three actuators 87 are controllable to fully control the orientation of the disc 85 and thereby the movement of the corresponding zone of the handling end portion.

In this way the electronic control of the longitudinal elements through linear actuators is reduced to the electronic control of either three or two such actuators which is less complicated than the full control of all longitudinal elements.

When expanding the idea of a system of having more than one system of longitudinal elements and having a corresponding number of flexible portions it is possible to even make more complicated curves.

During manufacture of a steerable instrument as described above one or more intermediate elements are incorporated between inner and outer cylindrical elements. This may be done in various ways. An intermediate cylindrical element can be provided over an inner cylindrical element or into an outer cylindrical element, after which the outer cylindrical element is provided over the intermediate cylindrical element or the inner cylindrical element is provided into the intermediate cylindrical element, respectively. Alternatively, the inner and outer cylindrical elements may be provided over one another, after which the intermediate cylindrical element is incorporated in between the inner and outer cylindrical elements. These provide some basic manners of assembling together the inner, intermediate and outer cylindrical elements when manufacturing a steerable instrument. One may vary on these manners described, and all such alternatives are within the scope of incorporating the intermediate cylindrical element between the inner and outer cylindrical elements.

To better be able to manufacture, handle and incorporate an intermediate cylindrical element between inner and outer cylindrical elements, adjacent longitudinal elements of the intermediate cylindrical element(s) are attached together by fracture or flexure elements. The fracture or flexure elements prevent that the intermediate element, before it is inserted into and/or shifted over another cylindrical element, loses its geometrical coherence and provides some rigidity to an intermediate element, which enhances easy manufacturing of the intermediate element and provides a better handling ability thereof.

In absence of fracture or flexure elements, the longitudinal elements would radially spring out and the cylindrical shape of the intermediate cylindrical element would be lost. Furthermore, the intermediate element would become very sloppy and difficult to handle. This may cause damage to the intermediate cylindrical element or the inner or outer cylindrical elements, and makes manufacturing of a steerable instrument very difficult and tedious.

FIGS. 8*a* to 16*b* show various embodiments of fracture or flexure elements 7 between adjacent longitudinal elements 4 of an intermediate cylindrical element 103. The embodiment of 11*a* and 11*b* generally is suitable as a flexible element to allow for longitudinal movement of the longitudinal elements while remaining in place, but can also be dimensioned such that that it fractures upon movement of the longitudinal elements or it can be removed by cutting during manufacture. The invention provides for a temporal (releasable) or flexible coupling by a flexure element between adjacent longitudinal elements. A releasable coupling may also be provided by application of a wax or glue or the like between adjacent longitudinal elements, as is indicated by dots of wax or glue 8 in FIG. 2*h*. The embodiments of a releasable or flexible coupling between adjacent longitudinal elements can be part of any of the embodiments described with reference to FIGS. 1 to 7*b*.

Figure 8A:
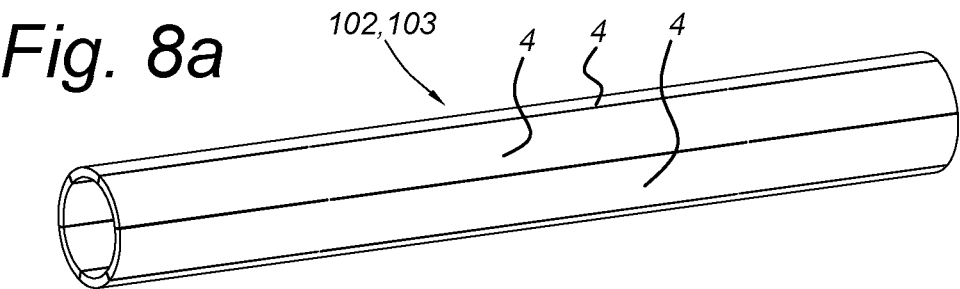
FIGS. 8a to 16b show various embodiments of details of intermediate cylindrical elements with fracture elements in perspective (the a figures) and side (the b figures) views, respectively.
Figure 8B:
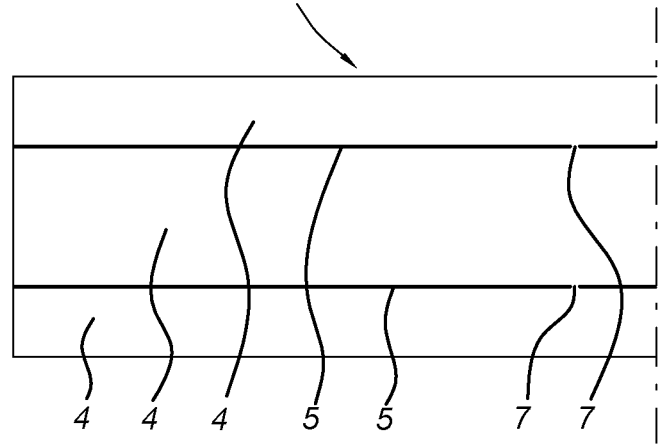

The fracture elements 7 shown in FIGS. 8*a* and 8*b* are small bridge elements crossing the slits 5 between adjacent elements. The slits may have been made by, for instance, laser cutting of the material of the intermediate cylindrical element 103. Some parts may be left uncut by the laser to provide the fracture elements 7 crossing the slits 5 at various locations distributed along the longitudinal elements 4. When the intermediate element has been incorporated between inner and outer cylindrical elements 101, 104 as shown, for instance, in FIGS. 2*c* and 2*d*, the longitudinal elements may be moved with respect to one another by movement of a flexible proximal portion 14, 15 to move a corresponding flexible distal portion 16, 17. The dimensions of the fracture element 7 are chosen such that they will easily fracture upon such movement when only little force is applied.

Figure 9A:
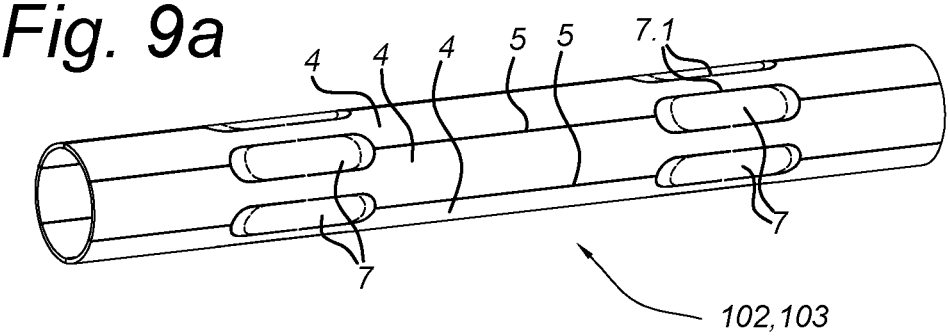
Figure 9B:
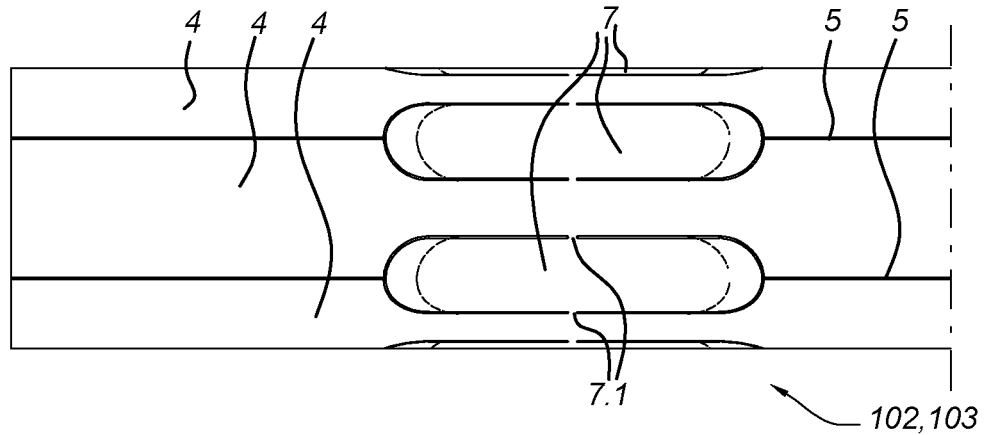

FIGS. 9*a* and 9*b* show an embodiment with fracture elements 7 having bridge elements 7.1 bridging slits 5. In the present embodiment a fracture element 7 attaches to adjacent longitudinal elements 4 by respective bridge parts 7.1. Several options are available for fracturing the bridge parts. When incorporating intermediate cylindrical element 103 between inner and outer cylindrical elements an appropriate force is applied to each fracture elements 7 such that the bridge parts 7.1 fracture and the fracture element is removed from the intermediate cylindrical element 103. The intermediate cylindrical element can be inserted in between inner and outer cylindrical elements until a position where one or more fracture elements 7 reach the inner and outer cylindrical elements. The fracture elements 7 are then removed from the intermediate cylindrical element, which is subsequently further inserted in between inner and outer cylindrical elements until a next position where a following set of one or more fracture elements reach the inner and/or outer cylindrical elements. The fracture elements are again removed and the process is repeated until the intermediate cylindrical element is fully inserted between inner and outer cylindrical elements.

Alternatively, the intermediate cylindrical element can be inserted within an outer cylindrical element, or over an inner cylindrical element without yet removing the fracture elements 7. The longitudinal elements 4 are then moved with respect to one another by moving a flexible proximal or distal part so as to fracture the fracture locations by shearing forces of bridge parts 7.1, which are then disconnected from the intermediate cylindrical element and will drop from the intermediate cylindrical element. When all fracture parts are removed the outer or inner cylindrical element, respectively, can be added.

In yet another alternative embodiment the fracture element 7 has been made shorter than the length of the gap in which it is located, as indicated by the dashed lines in FIGS. 9a and 9b. In such embodiment the intermediate cylindrical element can be inserted in between inner and outer cylindrical elements, after which the longitudinal elements 4 of the intermediate cylindrical elements can be moved with respect to one another to fracture the fracture locations of bridge parts 7.1. Since the fracture elements are shorter than the length of the gaps in which they are located, the fracture elements may remain in these gaps in an assembled state of inner, intermediate and outer cylindrical elements. The disconnected fracture elements 7 will not obstruct movement of the longitudinal elements 4 provided the length of the fracture elements 7 is short enough with respect to the length of the gap in which they are located.

Figure 10A:
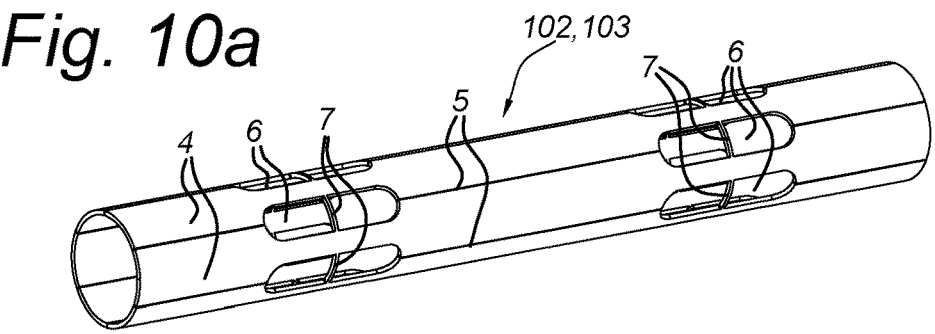
Figure 10B:
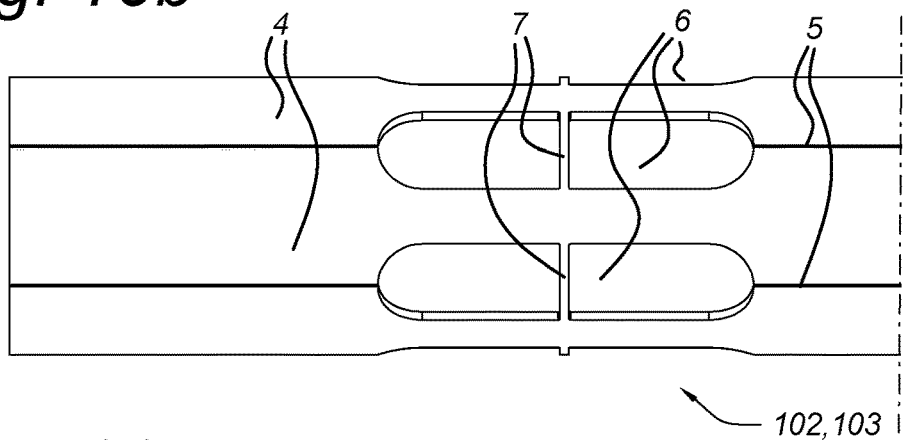

FIGS. 10a and 10b show an embodiment with slits 5 and gaps 6 between adjacent longitudinal elements 4 of an intermediate cylindrical element 103. The gaps 6 are an extension of the slits 5. Fracture elements 7 are provided in the gaps 6 and attach adjacent longitudinal elements 4. The fracture elements of the embodiment of FIGS. 10a and 10b have a linear and straight configuration. They cross the gap in a direction perpendicular to the slits such as to have a shortest length. The width of the gaps 6, in the present embodiment and other embodiments described, can correspond to 5-95% of the width of a longitudinal element as measured in a direction perpendicular to a longitudinal direction of the longitudinal element. This may correspond to a gap width in the range of 0.1-1 mm, but will be dependent on the actual dimensions of the longitudinal elements. The width of the gaps in the embodiment of FIGS. 10a and 10b corresponds to an angle of about 30 degrees around the longitudinal axis of the intermediate cylindrical element and to about 50% of the width of a longitudinal element. The width of the fracture element 7 of the FIGS. 10a and 10b embodiment is constant and a length over width ratio of the fracture element is larger than 4, especially larger than 8, and is 10 in the embodiment shown.

Figure 11A:
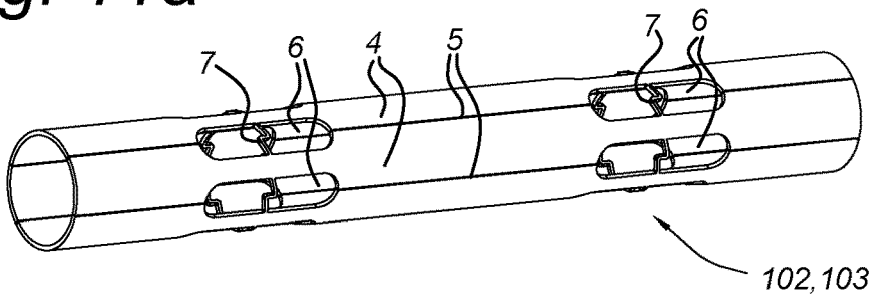
Figure 11B:
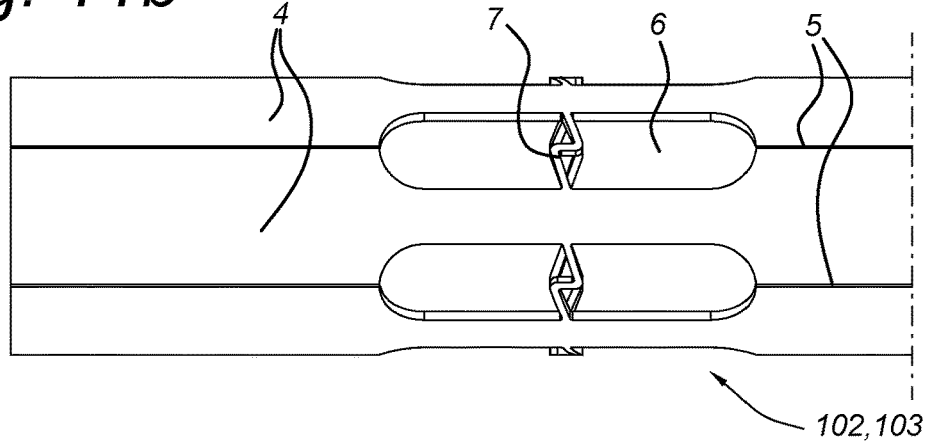

The embodiment shown in FIGS. 11a and 11b is equivalent to the one shown in FIGS. 10a and 10b. The elements 7 are, however, Z-shaped. Such Z-shape may provide flexibility to the element 7 so that it may remain in place and to provide a flexure element 7. The flexure element 7 will then allow longitudinal movement of the longitudinal elements, but restrict movement thereof in a radial direction. It is to be understood that other shapes than Z-shapes are possible to obtain the desired effect of this embodiment. Such other shapes may include S-shapes, a plurality of Z-shapes, a plurality of S-shapes, etcetera. However, the element 7 may also be shaped and dimensioned such that predetermined fracture locations near the attachments of the, in this case, fracture element 7 with the respective longitudinal elements 4. In the latter case the thickness and or width of the fracture element 7 should be such that it is rather rigid than flexible. It should be dimensioned such that is easily breaks, preferably at the locations of the attachment.

Figure 12A:
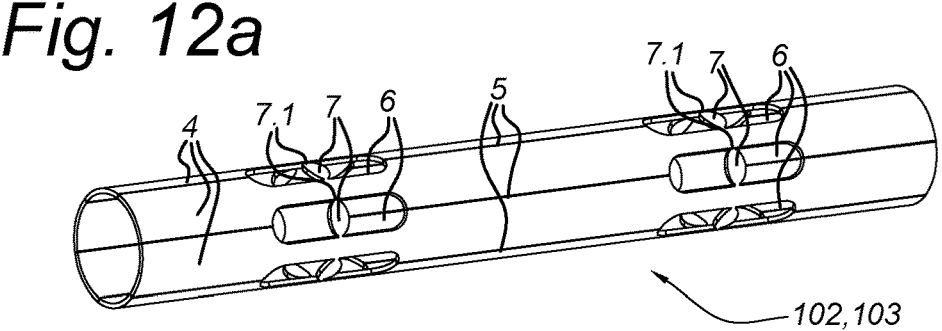
Figure 12B:
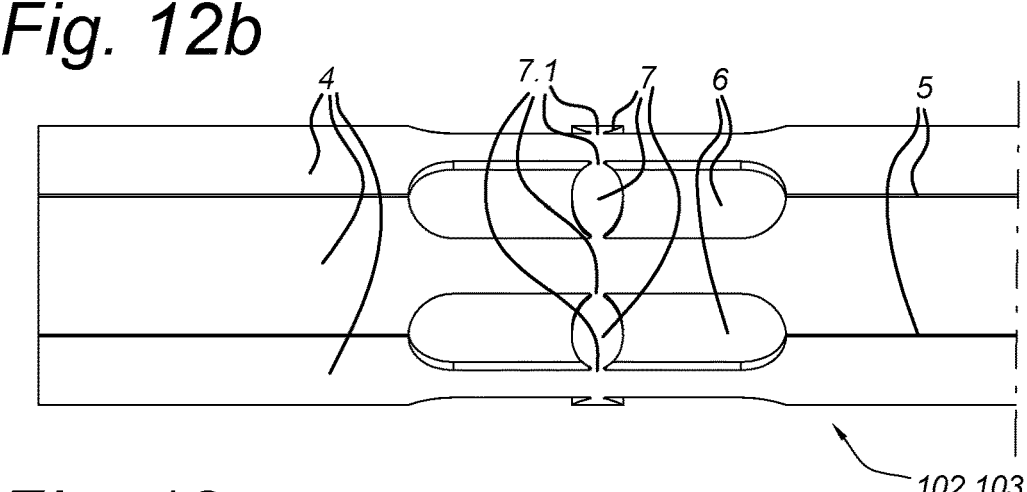

FIGS. 12a and 12b show yet another embodiment of an intermediate cylindrical element 103 with fracture elements 7. The fracture elements have a width in a longitudinal direction of the intermediate cylindrical element, and a length in a circumferential direction of the intermediate cylindrical element. Ends 7.1 of the fracture elements attach to adjacent longitudinal elements, each end to a respective one of the longitudinal elements 103. The width of the fracture elements decreases from a central area of the fracture elements along their lengths towards their ends such that the ends provide fracture locations. The fracture elements will fracture at these fracture locations at the ends 7.1 of the fracture elements when the longitudinal elements 4 are moved with respect to one another. The fracture element of FIGS. 12a and 12b has an elliptical shape and a width smaller than the length of the gap 6. The length of the gap 6 is measured in the longitudinal direction of the intermediate cylindrical element 103.

Figure 13A:
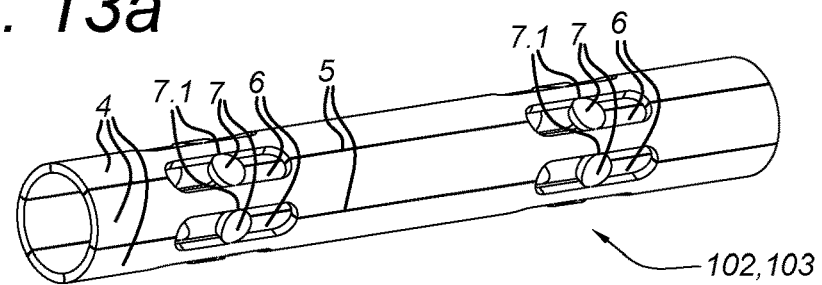
Figure 13B:
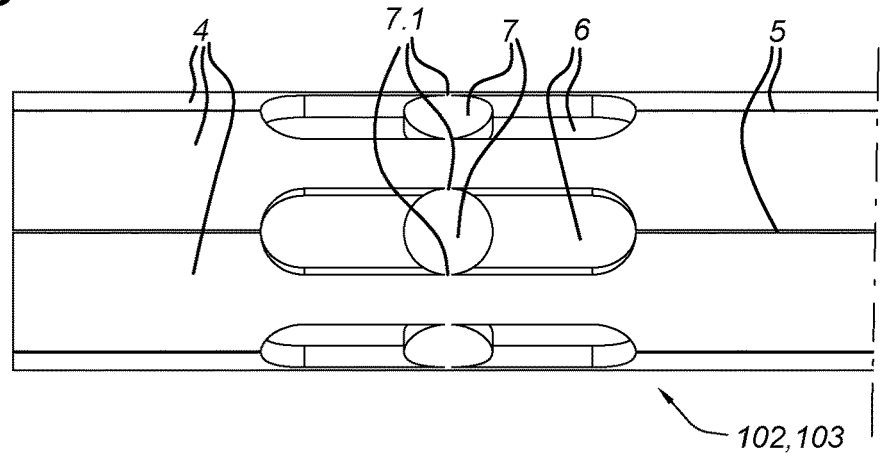

FIGS. 13a and 13b show an embodiment comparable to the one of FIGS. 12a and 12b. In this embodiment the fracture element has a circular shape. It is again attached at ends of fracture locations 7.1 to respective adjacent longitudinal elements.

In the embodiment of FIGS. 13a and 13b the fracture locations will break (fracture) due to a combination of bending forces and tension forces created by rolling off of the circular shaped fracture element along sides of the longitudinal elements. In general a fracture element 7 can be designed to have a shape such that one or more of shear forces, bending forces and tension forces act upon the fracture locations 7.1 of the fracture elements when adjacent longitudinal elements are moved relative to one another. Depending on the application a shape of the fracture elements can be chosen that it suits the specific purpose best.

Figure 14A:
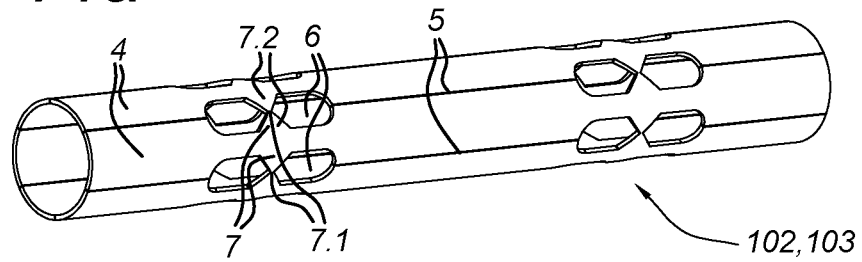
Figure 14B:
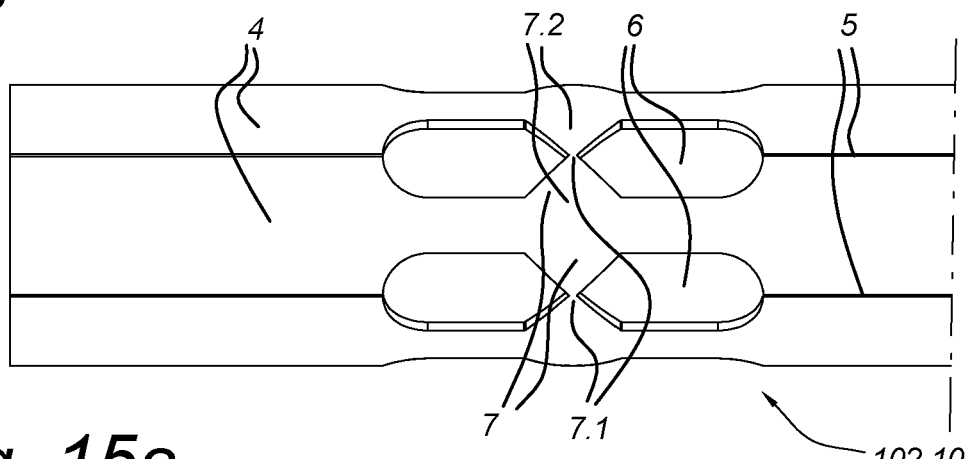
Figure 15A:
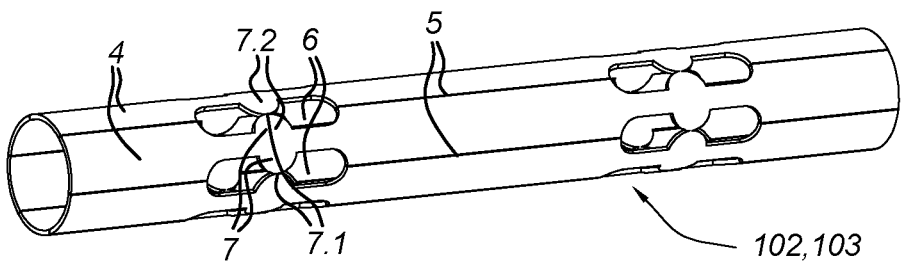
Figure 15B:
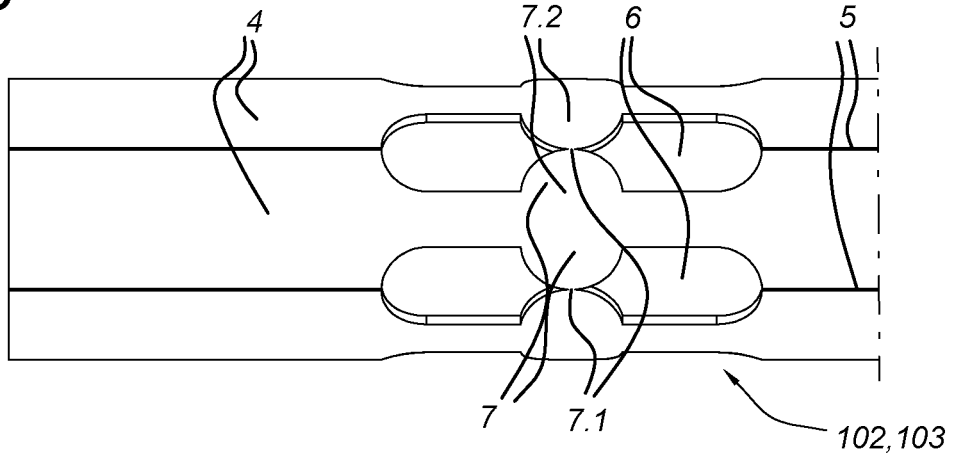

FIGS. 14a, 14b, 15a and 15c show embodiments of fracture elements with ends attaching to respective longitudinal elements 4, but a width of the fracture elements decreasing from the ends 7.2 of the fracture elements along their lengths towards a central area of the fracture elements, such that the central areas provide fracture locations 7.1. The fracture elements 7 of both these embodiments are hourglass shaped. In the embodiment of FIGS. 14a and 14b the fracture elements comprise triangular shapes attaching at their tops, and the embodiment of FIGS. 15a and 15b comprises two substantially semi-elliptical shapes attaching at their semi-elliptical circumference. The fracture locations 7.1 of this embodiment will fracture as a result of shearing forces when longitudinal elements 4 are moved relative to one another.

Figure 16A:
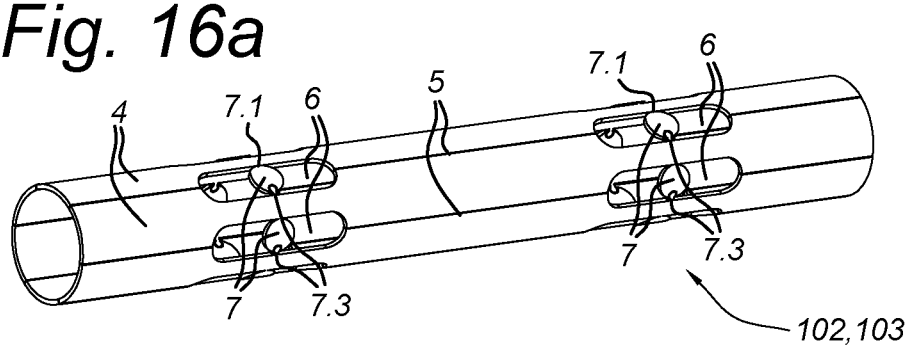
Figure 16B:
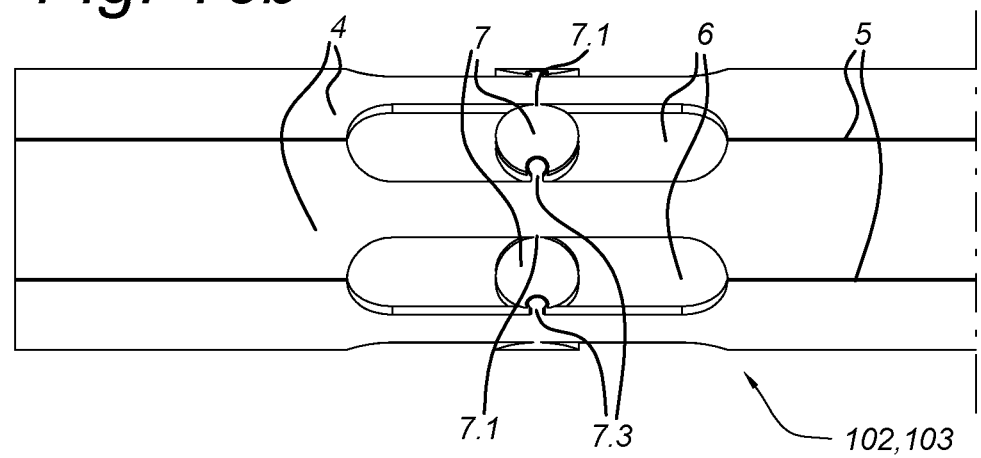

FIGS. 16a and 16b show an embodiment that is a variation of the one shown in FIGS. 13a and 13b. The fracture element 7 is at one end provided with a fracture location 7.1, while at the other end a flexure location 7.3 is provided. The flexure location 7.3 comprises a pin in socket connection. All force applied to longitudinal elements for fracturing the fracture elements is then concentrated on this one end 7.1, which results in less force being required to fracture the fracture element 7. In yet another variation flexure locations may be provided at both ends of an element 7 so as to provide a flexure element 7 between adjacent longitudinal elements. The variations described with reference to FIGS. 16a and 16b can be applied to embodiments of elements disclosed earlier.

In accordance with the present invention, fracture of the fracture elements 7, possibly at the fracture location(s) 7.1, should occur when the following condition is met. The longitudinal elements 4, 2338 are arranged such that they have a yield stress $\sigma_{y,le}$ and an ultimate tensile stress or $\sigma_{UTS,le}$. Moreover, each fracture element 7 is arranged such that is has a certain yield stress $\sigma_{y,fe}$ and an ultimate tensile stress a $\sigma_{UTS,fe}$. It is observed that in case the fracture elements are made of the same material as the longitudinal elements, the following applies:

$$\sigma_{y,le} = \sigma_{y,fe} \text{ and } \sigma_{UTS,le} = \sigma_{UTS,fe}$$

The condition to be met is that each fracture element 7 will fracture when adjacent longitudinal elements 4, 2338, to which such fracture element 7 is attached, are moved in a longitudinal direction relative to one another such as to develop a stress in each such fracture element 7 that is larger than or equal to the ultimate tensile stress $\sigma_{UTS,fe}$ of each individual fracture element 7, while, at the same time, the stress as developed in these adjacent longitudinal elements 4, 2338 remains lower than their own respective yield stresses $\sigma_{y,le}$. Stated otherwise in an equation:

$$\sigma_{act,le} \leq \sigma_{y,le} \text{ and } \sigma_{act,fe} \geq \sigma_{UTS,fe}$$

where $\sigma_{act,le}$ is the actual stress as developed in each one of the adjacent longitudinal elements 4, 2338 and $\sigma_{act,fe}$ is the actual stress as developed in each one of the fracture elements 7 caused by said relative movement of the adjacent longitudinal elements 4, 2338.

Note that the actual stress as developed in each one of the adjacent longitudinal elements 4, 2338 needs to be higher to meet the condition $\sigma_{act,fe} \geq \sigma_{UTS,fe}$ if the number of fracture elements 7 increases, such that it may be more difficult to meet the condition $\sigma_{act,le} \leq \sigma_{y,le}$. In order to meet a safety margin, the condition may be that once $\sigma_{act,fe} = \sigma_{UTS,fe}$ in each one of the fracture elements as caused by said relative movement of the adjacent longitudinal elements 4, 2338, then $\sigma_{act,le} \leq \alpha \cdot \sigma_{y,le}$, where $0.01 < \alpha \leq 0.8$, preferably $0.01 < \alpha \leq 0.5$.

FIG. 17 shows an assembly of two intermediate cylindrical elements 102, 103 provided between inner and outer cylindrical elements 101, 104. The elements are only partially shown so as to provide a view on other elements. Intermediate cylindrical element 103 has longitudinal elements 4 that are provided in a spiral configuration, while the longitudinal elements of intermediate cylindrical element 102 have a straight configuration. In other embodiment the longitudinal elements 4 may both have a straight or spiral configuration. It yet other embodiments the longitudinal elements 4 of the intermediate cylindrical elements may have yet other configurations that would suit the intended purpose. Both intermediate cylindrical elements 102, 103 are provided as well with fracture elements 7 in between adjacent longitudinal elements 4. The fracture elements 7 are of the embodiment described with reference to FIGS. 13a and 13b, but may be of any other appropriate embodiment. The fracture elements 7 are positioned such along the longitudinal elements that fracture elements of one intermediate cylindrical element will not interfere with fracture elements and their corresponding gaps of the adjacent intermediate cylindrical element. In general, the fracture elements are positioned such that they do not interfere with any part of adjacent cylindrical elements.

The invention claimed is:

1. A method for manufacturing a steerable instrument for endoscopic and/or invasive type applications, such as in surgery, the instrument comprising
   an elongated tubular body having a proximal end part, a distal end part and an intermediate part between proximal and distal end parts, the proximal end part having at least one actuation proximal zone, the distal end part having at least one flexible distal zone, and the elongated tubular body being configured such that a movement of an actuation proximal zone of the at least one actuation proximal zone is transferred to an associated flexible distal zone of the at least one flexible distal zone, which is associated with said actuation proximal zone of the at least one actuation proximal zone for a corresponding movement thereof,
   the elongated tubular body comprising an inner cylindrical element, an outer cylindrical element and at least one intermediate cylindrical element having longitudinal elements and provided between the inner and outer cylindrical elements, the inner, outer and intermediate cylindrical elements being coupled such that movement of said actuation proximal zone is transferred by the longitudinal elements of one of the intermediate cylindrical elements to said associated flexible distal zone,
   the method comprising
      providing the inner and outer cylindrical elements;
      providing an intermediate cylindrical element such that adjacent longitudinal elements are attached to one another at one or more positions distributed along a length of the longitudinal elements by one or more attachments arranged to restrict movement of the longitudinal elements in a radial direction of the intermediate cylindrical element; and
      incorporating the intermediate cylindrical element between the inner and outer cylindrical elements,
   wherein the one or more attachments are releasable attachments and the method comprises
      releasing the releasable attachments to allow relative movement of the longitudinal elements with respect to one another in a longitudinal direction of the longitudinal elements, the releasable attachments comprising fracture elements configured to allow fracture thereof for releasing the releasable attachment, the fracture elements being fractured after having incorporated the intermediate cylindrical element between inner and outer cylindrical elements by applying a force onto adjacent longitudinal elements such as to induce movement of the longitudinal elements with respect to one another and to fracture the fracture elements.

2. The method according to claim 1, wherein the fracture elements are shaped such as to provide one or more predetermined fracture locations where the fracture elements will fracture upon application of the force.

3. The method according to claim 1, wherein the force is applied to the longitudinal elements by applying another force force to said actuation proximal zone or said associated flexible distal zone.

4. The method according to claim 1, wherein the fracture elements are fractured, and optionally removed, when incorporating the intermediate cylindrical element between inner and outer cylindrical elements.

5. The method according to claim 1, wherein each fracture element is configured and arranged to fracture when adjacent longitudinal elements, to which each such fracture element is attached, are moved in a longitudinal direction relative to one another such as to develop an actual fracture element stress, $\sigma_{act,fe}$, in each such fracture element which is larger than or equal to an ultimate tensile stress, $\sigma_{UTS,fe}$, of each individual fracture element, while, at the same time, an actual longitudinal element stress, $\sigma_{act,le}$, as developed in each one of these adjacent longitudinal elements remains lower than their own respective yield stresses, $\sigma_{y,le}$, which can be stated in the equation:

$$\sigma_{act,le} \leq \sigma_{y,le} \text{ and } \sigma_{act,fe} \geq \sigma_{UTS,fe}.$$

6. The method according to claim 5, wherein the fracture elements are configured and arranged such that once $\sigma_{act,fe} = \sigma_{UTS,fe}$ in each one of the fracture elements as caused by said relative movement of the adjacent longitudinal elements, then $\sigma_{act,le} \leq \alpha \cdot \sigma_{y,le}$, where $0.01 < \alpha \leq 0.8$, preferably $0.01 < \alpha \leq 0.5$.

7. A cylindrical element for use in the method for manufacturing the steerable instrument for endoscopic and/or invasive type applications according to claim 1, the intermediate cylindrical element comprising longitudinal elements of which adjacent ones are attached by at least one of the one or more fracture elements at one or more positions distributed along a length of the longitudinal elements, wherein each fracture element is configured and arranged to fracture when adjacent longitudinal elements, to which each such fracture element is attached, are moved in a longitudinal direction relative to one another such as to develop an actual fracture element stress, $\sigma_{act,fe}$, in each such fracture element which is larger than or equal to an ultimate tensile stress, $\sigma_{UTS,fe}$, of each individual fracture element, while, at the same time, an actual longitudinal element stress, $\sigma_{act,le}$, as developed in each one of these adjacent longitudinal elements remains lower than their own respective yield stresses, $\sigma_{y,le}$, which can be stated in the equation:

$$\sigma_{act,le} \leq \sigma_{y,le} \text{ and } \sigma_{act,fe} \geq \sigma_{UTS,fe}.$$

8. The cylindrical element according to claim 7, wherein the fracture elements are configured and arranged such that once $\sigma_{act,fe} = \sigma_{UTS,fe}$ in each one of the fracture elements as caused by said relative movement of the adjacent longitudinal elements, then $\sigma_{act,le} \leq \alpha \cdot \sigma_{y,le}$, where $0.01 < \alpha \leq 0.8$, preferably $0.01 < \alpha \leq 0.5$.

9. The cylindrical element according to claim 7, wherein adjacent longitudinal elements are separated by slits, and the one or more slits are bridged by at least one of the one or more fracture elements at the one or more positions distributed along the length of the longitudinal elements.

10. The cylindrical element according to claim 9, wherein the slit is dimensioned such that movement of a longitudinal element of the longitudinal elements is guided by adjacent longitudinal elements when provided in the steerable instrument.

11. The cylindrical element according to claim 7, wherein a gap is provided between adjacent longitudinal elements along at least part of a length of the adjacent longitudinal elements, and the at least one of one or more fracture elements is provided in the gap.

12. The cylindrical element according to claim 11, wherein a width of the gap corresponds to 5%-95% of the width of the longitudinal elements as measured in a direction perpendicular to the longitudinal direction of the longitudinal elements.

13. The cylindrical element according to claim 7, wherein the at least one or more fracture elements have a substantially constant width in a longitudinal direction of the longitudinal elements.

14. The cylindrical element according to claim 7, wherein the at least one of one or more fracture elements have at least one of the following shapes: one or more Z-shapes and one or more S-shapes.

15. The cylindrical element according to claim 7, wherein the at least one or more fracture elements are shaped such as to provide one or more predetermined fracture locations where the at least one or more fracture elements will fracture upon application of the force.

16. The cylindrical element according to claim 15, wherein the at least one or more fracture elements have a width in a longitudinal direction of the longitudinal elements, a length in a direction perpendicular to the longitudinal direction of the longitudinal elements and ends, each end being attached to a respective one of the adjacent longitudinal elements, the width of the at least one or more fracture elements decreasing from a central area of the fracture elements along their lengths towards their ends such that the ends provide fracture locations.

17. The cylindrical element according to claim 16, wherein the at least one or more fracture elements have a substantially elliptical shape.

18. The cylindrical element according to claim 16, wherein the at least one or more fracture elements have a substantially circular shape.

19. The cylindrical element according to claim 15, wherein the at least one or more fracture elements have a width in a longitudinal direction of the longitudinal elements, a length in a direction perpendicular to the longitudinal direction of the longitudinal elements and ends, each end being attached to a respective one of the adjacent longitudinal elements, the width of the at least one or more fracture elements decreasing from the ends of the at least one or more fracture elements along their lengths towards a central area of the at least one or more fracture elements, such that the central area provides a fracture location.

20. The cylindrical element according to claim 19, wherein the at least one or more fracture elements are substantially hour-glass shaped.

21. The cylindrical element according to claim 19, wherein the at least one or more fracture elements comprise two substantially triangular shaped members attached at their tops.

22. The cylindrical element according to claim 19, wherein the at least one or more fracture elements comprise two substantially semi-elliptical shaped members attached at their semi-elliptical circumference.

23. The cylindrical element according to claim 19, wherein the at least one or more fracture elements comprise two substantially semi-circular shaped members attached at their semi-circular circumference.

24. A steerable instrument for endoscopic and/or invasive type applications, the instrument comprising an elongated tubular body having a proximal end part, a distal end part and an intermediate part between proximal and distal end parts, the proximal end part having at least one actuation proximal zone, the distal end part having at least one flexible distal zone, and the elongated tubular body being configured such that a movement of an actuation proximal zone of the at least one actuation proximal zone is transferred to an associated flexible distal zone of the at least one flexible distal zone, which is associated with said actuation proximal zone of the at least one actuation proximal zone for a corresponding movement thereof, the elongated tubular body comprising an inner cylindrical element, an outer cylindrical element and at least one intermediate cylindrical element having longitudinal elements and provided between the inner and outer cylindrical elements, the inner, outer and intermediate cylindrical elements being coupled such that movement of an actuation proximal zone is transferred by the longitudinal elements of one of the intermediate cylindrical elements to a corresponding flexible distal zone, and the at least one intermediate cylindrical element being a cylindrical element according to claim 7 and having the fracture elements that are fractured, removed or not yet fractured.

25. The steerable instrument according to claim 24, wherein the fracture elements are distributed such along the length of the intermediate cylindrical element that the fracture elements do not interfere with one or more parts of an adjacent cylindrical element.

26. The steerable instrument according to claim 24, wherein at least two adjacent intermediate cylindrical elements are provided, and the fracture elements are distributed such along the length of the intermediate cylindrical elements that a fracture element of the fracture elements of one intermediate cylindrical element does not interfere with one or more fracture elements of an adjacent intermediate cylindrical element.

27. A method of manufacturing a steerable instrument for endoscopic and/or invasive type applications, the method comprising:

incorporating a cylindrical element between an outer cylindrical element and an inner cylindrical element such as to form the steerable instrument, the cylindrical element comprising a first element and a second element which are adjacent to one another and are attached by at least one fracture element, the first element having a first yield stress and the second element having a second yield stress, the at least one fracture element having an ultimate tensile stress, the method comprising:

fracturing the at least one fracture element by moving the adjacent first and second elements relative to one another such as to develop an actual fracture element stress in the at least one fracture element which is larger than or equal to the ultimate tensile stress of the at least one fracture element, while, at the same time, developing an actual first element stress in the first element which remains lower than the first yield stress and developing an actual second element stress in the second element which remains lower than the second yield stress.

28. A cylindrical element for use in the method for manufacturing a steerable instrument for endoscopic and/or invasive type applications according to claim 27, the cylindrical element comprising a first element and a second element which are adjacent to one another and are attached by at least one fracture element, the first element having a first yield stress and the second element having a second yield stress, the at least one fracture element having an ultimate tensile stress, wherein the at least one fracture element is configured and arranged to fracture when the adjacent first and second elements are moved relative to one another such as to develop an actual fracture element stress in the at least one fracture element which is larger than or equal to the ultimate tensile stress of the at least one fracture element, while, at the same time, an actual first element stress as developed in the first element remains lower than the first yield stress and an actual second element stress as developed in the second element remains lower than the second yield stress.

\* \* \* \* \*